US007186521B2

(12) United States Patent
Lynch et al.

(10) Patent No.: US 7,186,521 B2
(45) Date of Patent: Mar. 6, 2007

(54) DETERMINING THE EFFECT OF A SUBSTANCE ON SEQUESTRATION, UPTAKE, AND ACCUMULATION OF AMYLOID IN BRAIN CELLS

(75) Inventors: Gary Lynch, Irvine, CA (US); Xiaoning Bi, Irvine, CA (US); Christine M. Gall, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 75 days.

(21) Appl. No.: 09/961,381

(22) Filed: Sep. 25, 2001

(65) Prior Publication Data

US 2002/0061515 A1 May 23, 2002

Related U.S. Application Data

(60) Provisional application No. 60/235,374, filed on Sep. 25, 2000.

(51) Int. Cl.
*C12Q 1/02* (2006.01)
*G01N 33/53* (2006.01)
*C12N 5/00* (2006.01)

(52) U.S. Cl. .................... 435/29; 435/7.1; 435/325
(58) Field of Classification Search ............... 435/4, 435/29, 325, 366, 7.21, 7.1; 800/3, 8, 12; 514/12
See application file for complete search history.

(56) References Cited

U.S. PATENT DOCUMENTS

| 4,366,241 | A | 12/1982 | Tom et al. |
| 4,376,110 | A | 3/1983 | David et al. |
| 4,517,288 | A | 5/1985 | Giegel et al. |
| 4,837,168 | A | 6/1989 | de Jaeger et al. |
| 5,010,175 | A | 4/1991 | Rutter et al. |
| 5,464,764 | A | 11/1995 | Capecchi et al. |
| 5,539,083 | A | 7/1996 | Cook et al. |
| 5,627,059 | A | 5/1997 | Capecchi et al. |
| 5,767,337 | A | 6/1998 | Roses et al. |
| 5,830,678 | A | 11/1998 | Carter |
| 5,877,399 | A | 3/1999 | Hsiao et al. |
| 6,046,381 | A | 4/2000 | Mucke et al. |
| 6,120,991 | A | 9/2000 | Carter et al. |
| 2002/0048746 | A1 | 4/2002 | Lynch et al. |

FOREIGN PATENT DOCUMENTS

WO  WO 92/00091 A1  1/1992
WO  WO 93/20242 A1  10/1993

OTHER PUBLICATIONS

Harris-White, M. E. et al. Effects of Transforming Growth Factor-Beta (Isoforms 1-3) on Amyloid-Beta Depostion, Inflammation and Cell Targeting in Organotypic Hippocampal Slice Cultures. The Journal of Neuroscience. Dec. 1998, vol. 18, pp. 10366-10374.*

Matter et al. The Alpha5Beta1 Integrin Mediates Elimination of Amyloid-Beta Peptide and Protects Against Apoptosis. Journal of Cell Biology. May 18, 1998, vol. 141, pp. 1019-1030.*

Hab et al. Physical Interaction of ApoE with Amyloid Precursor Protein Independent of the Amyloid A-Beta Region In Vitro Journal of Biolog. Chem. May 29, 1998, vol. 273, pp. 13892-13897.*

Scarborough et al, Journal of Biological Chemistry, 266:9359-9362, 1991.*

Hass et al, Journal of Biological Chemistry, 273:13892-13897, 1998.*

Akiyama, H., et al., "Inflammation and Alzheimer's disease," *Neurobiol. Aging* 21:383-421, Elsevier Science (May-Jun. 2000).

Backstrom, J.R., et al., "Matrix Metalloproteinase-9 (MMP-9) Is Synthesized in Neurons of the Human Hippocampus and Is Capable of Degrading the Amyloid-β Peptide (1-40)," *J. Neurosci.* 16:7910-7919, Society for Neuroscience (1996).

Bahr, B.A., et al., "Stable Maintenance of Glutamate Receptors and Other Synaptic Components in Long-Term Hippocampal Slices," *Hippocampus* 5:425-439, Wiley-Liss (1995).

Bahr, B.A., et al., "Amyloid β Protein is Internalized Selectively by Hippocampal Field CA1 and Causes Neurons to Accumulate Amyloidogenic Carboxyterminal Fragments of the Amyloid Precursor Protein," *J. Comp. Neurol.* 397:139-147, Wiley-Liss (1998).

Bahr, B., and Lynch, G., "Purification of an Arg-Gly-Asp selective matrix receptor from brain synaptic plasma membranes," *Biochem. J.* 281:137-142, The Biochemical Society/Portland Press (1992).

Bahr, B.A., et al., "Fibronectin binding by brain synaptosomal membranes may not involve conventional integrins," *Neuroreport* 2:13-16, Rapid Communications of Oxford (1991).

Bahr, B.A., et al., "Arg-Gly-Asp-Ser-Selective Adhesion and the Stabilization of Long-Term Potentiation: Pharmacological Studies and the Characterization of a Candidate Matrix Receptor," *J. Neurosci.* 17:1320-1329, Society for Neuroscience (1997).

Bahr, B.A., "Integrin-Type Signaling Has a Distinct Influence on NMDA-Induced Cytoskeletal Disassembly," *J. Neurosci. Res.* 59:827-832, Wiley-Liss (Mar. 2000).

(Continued)

*Primary Examiner*—Deborah Crouch
(74) *Attorney, Agent, or Firm*—Sterne, Kessler, Goldstein & Fox P.L.L.C.

(57) ABSTRACT

The present invention provides brain cells, such as normal brain cells, apolipoprotein E deficient brain cells, or apoE4 containing brain cells, that are treated with a compound which can modulate integrins and/or integrin receptors to produce increased sequestration of and/or accumulation of and/or uptake of Aβ, and/or changes in cathepsin D content and/or lysosomal dysfunction, and/or microglia activation in the brain cells. The present invention also provides methods for producing such cells and methods for using the cells for screening an agent or substance that modulates the sequestration of and/or accumulation of and/or uptake of Aβ, and/or lysosomal dysfunction, and/or changes in cathepsin D content and/or microglia activation in the brain cells. The method further provides a new therapeutic target, antagonism of glutamate receptors, for the treatment of neurodegenerative diseases which are characterized by inter alia, abnormal amyloid uptake and/or accumulation.

26 Claims, 7 Drawing Sheets

OTHER PUBLICATIONS

Bard, F., et al., "Peripherally administered antibodies against amyloid β-peptide enter the central nervous system and reduce pathology in a mouse model of Alzheimer disease," *Nat. Med.* 6:916-919, Nature America Inc. (Aug. 2000).

Barrett, A.J., and Kirschke, H., "Cathepsin B, Cathepsin H, and Cathepsin L," *Meth. Enzymol.* 80:535-561, Academic Press (1981).

Beattie, E.C., et al., "Regulation of AMPA receptor endocytosis by a signaling mechanism shared with LTD," *Nat. Neurosci.* 3:1291-1300, Nature America Inc. (Dec. 2000).

Bednarski, E., and Lynch, G., "Cytosolic Proteolysis of τ by Cathepsin D in Hippocampus Following Suppression of Cathepsins B and L," *J. Neurochem.* 67:1846-1855, Lippincott-Raven Publishers (1996).

Bednarski, E., and Lynch, G., "Selective suppression of cathepsin L results from elevations in lysosomal pH and is followed by proteolysis of tau protein," *NeuroReport* 9:2089-2094, Rapid Science (1998).

Bi, X., et al., "Polarized Distribution of α5 Integrin in Dendrites of Hippocampal and Cortical Neurons," *J. Comp. Neurol.* 435:184-193, Wiley-Liss (Jun. 2001).

Bi, X., et al., "Novel Cathepsin D Inhibitors Block the Formation of Hyperphosphorylated Tau Fragments in Hippocampus," *J. Neurochem.* 74:1469-1477, Lippincott Williams & Wilkins (Apr. 2000).

Brion, J.-P., et al., "Neurofilament Monoclonal Antibodies RT97 and 8D8 Recognize Different Modified Epitopes in Paired Helical Filament-τ in Alzheimer's Disease," *J. Neurochem.* 60:1372-1382, Raven Press (1993).

Bruce, A.J., et al., "β-Amyloid toxicity in organotypic hippocampal cultures: Protection by EUK-8, a synthetic catalytic free radical scavenger," *Proc. Natl. Acad. Sci. USA* 93:2312-2316, National Academy of Sciences (1996).

Burkin, D.J., et al., "A Functional Role for Specific Spliced Variants of the α7β1 Integrin in Acetylcholine Receptor Clustering," *J. Cell Biol.* 143:1067-1075, The Rockefeller University Press (1998).

Burnashev, N., et al., "Control of Asparagine Residues of Calcium Permeability and Magnesium Blockade in the NMDA Receptor," *Science* 257:1415-1419, American Association for the Advancement of Science (1992).

Busciglio, J., et al., "Generation of β-amyloid in the secretory pathway in neuronal and nonneuronal cells," *Proc. Natl. Acad. Sci. USA* 90:2092-2096, National Academy of Sciences (1993).

Callahan, L.M., et al., "Quantitative Decrease in Synaptophysin Message Expression and Increase in Cathepsin D Message Expression in Alzheimer Disease Neurons Containing Neurofibrillary Tangles," *J. Neuropathol. Exp. Neurol.* 58:275-287, American Association of Neuropathologists (Mar. 1999).

Carroll, R.C., et al., "Dynamin-dependent endocytosis of ionotropic glutamate receptors," *Proc. Natl. Acad. Sci. USA* 96:14112-14117, National Academy of Sciences (Nov. 1999).

Caswell, M.D., et al., "The amyloid β-protein precursor of Alzheimer's disease is degraded extracellularly by a Kunitz protease inhibitor domain-sensitive trypsin-like serine protease in cultures of chick sympathetic neurons," *Eur. J. Biochem.* 266:509-516, Blackwell Science (Dec. 1999).

Cataldo, A.M., et al., "Gene Expression and Cellular Content of Cathepsin D in Alzheimer's Disease Brain: Evidence for Early Up-Regulation of the Endosomal-Lysosomal System," *Neuron* 14:671-680, Cell Press (1995).

Chavis, P., and Westbrook, G., "Integrins mediate functional pre- and postsynaptic maturation at a hippocampal synapse," *Nature* 411:317-321, Nature Publishing Group (May 2001).

Chazot, P.L., "CP-101606," *Curr. Opin. Investig. Drugs* 1:370-374, PharmaPress (Nov. 2000).

Chen, C., et al., "'Analogous' Organic Synthesis of Small-Compound Libraries: Validation of Combinatorial Chemistry in Small-Molecule Synthesis," *J. Am. Chem. Soc.* 116:2661-2662, American Chemical Society (1994).

Chun, D., et al., "Evidence that Integrins Contribute to Multiple Stages in the Consolidation of Long Term Potentiation in Rat Hippocampus," *Neurosci.* 105:815-829, Elsevier Science (Aug. 2001).

Cotran, R.S., et al., "Forebrain Anomalies," in *Robbins Pathologic Basis of Disease*, 6th ed., Schmitt, B., ed., W.B. Saunders Co., Philadelphia, PA, p. 1300-1301 (1998).

Cotran, R.S., et al., "Neurofibrillary tangles," in *Robbins Pathologic Basis of Disease*, 6th ed., Schmitt, B., ed., W.B. Saunders Co., Philadelphia, PA, p. 1330 (1998).

Cras, P., et al., "Microglia are associated with the extracellular neurofibrillary tangles of Alzheimer disease," *Brain Res.* 558:312-314, Elsevier Science B.V. (1991).

Dunah, A.W., et al., "α-Actinin-2 in rat striatum: localization and interaction with NMDA glutamate receptor subunits," *Brain Res. Mol. Brain Res.* 79:77-87, Elsevier Science B.V. (Jun. 2000).

Ehlers, M.D., "Reinsertion or Degradation of AMPA Receptors Determined Activity-Dependent Endocytic Sorting," *Neuron* 28:511-525, Cell Press (Nov. 2000).

Fox, N., et al., "Seeing what Alzheimer saw-with magnetic resonance microscopy," *Nat. Med.* 6:20-21, Nature America (Jan. 2000).

Frenkel, D., et al., "Immunization against Alzheimer's β-amyloid plaques via EFRH phage administration," *Proc. Natl. Acad. Sci. USA* 97:11455-11459, National Academy of Sciences (Oct. 2000).

Games, D., et al., "Lack of Alzheimer Pathology After β-Amyloid Protein Injections in Rat Brain," *Neurobiol. Aging* 13:569-576, Pergamon Press (1992).

Ghiso, J., et al., "A 109-amino-acid C-terminal fragment of Alzheimer's-disease amyloid precursor protein contains a sequence, -RHDS-, that promotes cell adhesion," *Biochem. J.* 288:1053-1059, Portland Press (1992).

Ginsberg, S.D., et al., "Expression Profile of Transcripts in Alzheimer's Disease Tangle-Bearing CA1 Neurons," *Ann. Neurol.* 48:77-87, Lippincott Williams & Wilkins (Jul. 2000).

Gordon, I., et al., "Memory deficits and cholinergic impairments in apolipoprotein E-deficient mice," *Neurosci. Lett.* 199:1-4, Elsevier Science Ireland (1995).

Gottlieb, T.A., et al., "Actin Microfilaments Play a Critical Role in Endocytosis at the Apical but not the Basolateral Surface of Polarized Epithelial Cells," *J. Cell Biol.* 120:695-710, The Rockefeller University Press (1993).

Gouras, G.K., et al., "Intraneuronal Aβ42 Accumulation in Human Brain," *Am. J. Pathol.* 156:15-20, American Society for Investigative Pathology (Jan. 2000).

Guénette, S.Y., and Tanzi, R.E., "Progress toward valid transgenic mouse models for Alzheimer's disease," *Neurobiol. Aging* 20:201-211, Elsevier Science (Mar.-Apr. 1999).

Haass, C., et al., "Mutations Associated with a Locus for Familial Alzheimer's Disease Result in Alternative Processing of Amyloid β-Protein Precursor," *J. Biol. Chem.* 269:17741-17748, The American Society for Biochemistry and Molecular Biology (1994).

Haass, C., et al., "Targeting of cell-surface β-amyloid precursor protein to lysosomes: alternative processing into amyloid-bearing fragments," *Nature* 357:500-503, Macmillan Magazines (1992).

Harper, J.D., and Lansbury, Jr., P.T., "Models of Amyloid Seeding in Alzheimer's Disease and Scrapie: Mechanistic Truths and Physiological Consequences of the Time-Dependent Solubility of Amyloid Proteins," *Annu .Rev. Biochem.* 66:385-407, Annual Reviews Inc. (1997).

Harris-White, M.E., et al., "Effects of Transforming Growth Factor-β (Isoforms 1-3) on Amyloid-β Deposition, Inflammation, and Cell Targeting Organotypic Hippocampal Slice Cultures," *J. Neurosci* 18:10366-10374, Society for Neuroscience (1998).

Hoffman, K.B., et al., "β-Amyloid increases cathepsin D levels in hippocampus," *Neurosci. Lett.* 250:75-78, Elsevier Science Ireland (1998).

Hsia, A.Y., et al., "Plaque-independent disruption of neural circuits in Alzheimer's disease mouse models," *Proc. Natl. Acad. Sci. USA* 96:3228-3233, National Academy of Sciences (Mar. 1999).

Huang, T.-F., "What have snakes taught us about integrins," *Cell. Mol. Life Sci.* 54:527-540, Birkhäuser Verlag (1998).

Huse, W.D., et al., "Generation of a Large Combinatorial Library of the Immunoglobulin Repertoire in Phage Lambda," *Science* 246:1275-1281, American Association for the Advancement of Science (1989).

Isberg, R.R., and Tran Van Nhieu, G., "Binding and internalization of microorganisms by integrin receptors," *Trends Microbiol.* 2:10-14, Elsevier Science (1994).

Iwata, N., et al., "Identification of the major $A\beta_{1-42}$-degrading catabolic pathway in brain parenchyma: Suppression leads to biochemical and pathological deposition," *Nat. Med.* 6:143-150, Nature America Inc. (Feb. 2000).

Janus, C., et al., "Transgenic mouse models of Alzheimer's disease," *Biochim. Biophys. Acta* 1502:63-75, Elsevier Science B.V. (Jul. 2000).

Kang, J., et al., "The precursor of Alzheimer's disease amyloid A4 protein resembles a cell-surface receptor," *Nature* 325:733-736, Macmillan Journals (1987).

Kato, H., et al., "Graded expression of immunomolecules on activated microglia in the hippocampus following ischemic in a rat model of ischemic tolerance," *Brain Res.* 694:85-93, Elsevier Science B.V. (1995).

Köhler, G., and Milstein, C., "Continuous cultures of fused cells secreting antibody of predefined specificity," *Nature* 256:495-497, Macmillan Journals (1975).

Kuo, Y.-M., et al., "Water-soluble Aβ (N-40, N-42) Oligomers in Normal and Alzheimer Disease Brains," *J. Biol. Chem.* 271:4077-4081, The American Society for Biochemistry and Molecular Biology (1996).

Labat-Robert, J., "Cell-Matrix Interaction, Alterations with Aging, Involvement in Angiogenesis," *Pathol. Biol. (Paris)* 46:527-533, Expansion Scientifique Francaise (1998).

Le Varlet, B., et al., "Age-Related Functional and Structural Changes in Human Dermo-Epidermal Junction Components," *J. Investig. Dermatol. Symp. Proc.* 3:172-179, The Society for Investigative Dermatology, Inc. (1998).

Marsh, M., and McMahon, H.T., "The Structural Era of Endocytosis," *Science* 285:215-220, American Association for the Advancement of Science (Jul. 1999).

Matter, M.L., et al., "The α5β1 Integrin Mediates Elimination of Amyloid-β Peptide and Protects Against Apoptosis," *J. Cell. Biol.* 141:1019-1030, The Rockefeller University Press (1998).

Miller, D.L., et al., "Peptide Compositions of the Cerebrovascular and Senile Plaque Core Amyloid Deposits of Alzheimer's Disease," *Arch. Biochem. Biophys.* 301:41-52, Academic Press (1993).

Morgan, D., et al., "Aβ peptide vaccination prevents memory loss in an animal model of Alzheimer's disease," *Nature* 408:982-985, Nature Publishing Group (Dec. 2000).

Morris, J.C., "The Clinical Dementia Rating (CDR): Current version and scoring rules," *Neurology* 43:2412-2414, Advanstar Communications (1993).

Mucke, L., et al., "High-Level Neuronal Expression of $A\beta_{1-42}$ in Wild-Type Human Amyloid Protein Precursor Transgenic Mice: Synaptotoxicity without Plaque Formation," *J. Neurosci.* 20:4050-4058, Society for Neuroscience (Jun. 2000).

Mueller, A.L., et al., "NPS 1506, A Novel NMDA Receptor Antagonist and Neuroprotectant," *Ann. N.Y. Acad. Sci.* 890:450-457, New York Academy of Sciences (Dec. 1999).

Muller, D., et al., "Time course of synaptic development in hippocampal organotypic cultures," *Dev. Brain Res.* 71:93-100, Elsevier Science B.V. (1993).

Murphy, Jr., G.M., et al., "Expression of Macrophage Colony-Stimulating Factor receptor Is Increased in the $A\beta PP^{V717F}$ Transgenic Mouse Model of Alzheimer's Disease," *Am. J. Pathol.* 157:895-904, American Soiety for Investigative Pathology (Sep. 2000).

Nakanishi, H., et al., "Age-Related Changes in Activities and Localizations of Cathepsins D, E, B, and L in the Rat Brain Tissues," *Exp. Neurol.* 126:119-128, Academic Press (1994).

Nathan, B.P., et al., "Apolipoprotein E3- and E4-Induced Differences in Neurite Outgrowth Are Associated with Differences in the Subcellular Localization of Apolipoprotein E," *Soc. Neurosci.* 20(Part 2):1033, Abs. No. 421.5, Society for Neuroscience (1994).

NCBI Entrez, Genbank Report, Accession No. D00466, Rajavashisth, T.B., et al. (1993).

NCBI Entrez, Genbank Report, Accession No. M10065, Das, H.K., et al. (1993).

Nemerow, G.R., and Stewart, P.L., "Role of $\alpha_v$ Integrins in Adenovirus Cell Entry and Gene Delivery," *Microbiol. Mol. Biol. Rev.* 63:725-734, American Society for Microbiology (Sep. 1999).

Palmer, G.C., "Neuroprotection by NMDA Receptor Antagonists in a Variety of Neuropathologies," *Curr. Drug Targets* 2:241-271, Bentham Science Publsihers (Sep. 2001).

Perlmutter, L.S., et al., "Morphological association between microglia and senile plaque amyloid in Alzheimer's disease," *Neurosci. Lett.* 119:32-36, Elsevier Scientific Publishers Ireland (1990).

Peterson, R.C., et al., "Apolipoprotein E Status as a Predictor of the Development of Alzheimer's Disease in Memory-Impaired Individuals," *J. Am. Med. Assoc.* 273:1274-1278, American Medical Association (1995).

Pierschbacher, M.D., and Ruoslahti, E., "Cell attachment activity of fibronectin can be duplicated by small synthetic fragments of the molecule," *Nature* 304:30-33, Macmillan Journals (1984).

Pinkstaff, J.K., et al., "Integrin Subunit Gene Expression Is Regionally Differentiated in Adult Brain," *J. Neurosci.* 19:1541-1556, Society for Neuroscience (Mar. 1999).

Plump, A.S., et al., "Severe Hypercholesterolemia and Atherosclerosis in Apolipoprotein E-Deficient Mice Created by Homologous Recombination in ES Cells," *Cell* 71:343-353, Cell Press (1992).

Podlisny, M.B., et al., "Microinjection of Synthetic Amyloid β-Protein in Monkey Cerebral Cortex Fails to Produce Acute Neurotoxicity," *Am. J. Pathol.* 142:17-24, American Society for Investigative Pathology (1993).

Porter, J.C., and Hogg, N., "Integrins take partners: cross-talk between integrins and other membrane receptors," *Trends Cell Biol.* 8:390-396, Elsevier Science (1998).

Proescholdt, M., et al., "Neuroprotection of $S(+)$ ketamine isomer in global forebrain ischemia," *Brain Res.* 904:245-251, Elsevier Science B.V. (Jun. 2001).

Qiu, W.Q., et al., "Insulin-degrading Enzyme Regulates Extracellular Levels of Amyloid β-Protein by Degradation," *J. Biol. Chem.* 273:32730-32738, The American Society for Biochemistry and Molecular Biology (1998).

Rao, V.L.R., et al., "Neuroprotection by memantine, a non-competitive NMDA receptor antagonist after traumatic brain injury in rats," *Brain Res.* 911:96-100, Elsevier Science B.V. (Aug. 2001).

Ruoslahti, E., "RGD and Other Recognition Sequences for Integrins," *Annu. Rev. Cell Dev. Biol.* 12:697-715, Annual Reviews Inc. (1996).

Sabo, S., et al., "Interaction of beta-amyloid peptides with integrins in a human nerve cell line," *Neurosci. Lett.* 184:25-28, Elsevier Science Ireland (1995).

Schenk, D., et al., "Immunization with amyloid-β attenuates Alzheimer-disease-like pathology in the PDAPP mouse," *Nature* 400:173-177, Macmillan Magazines (Jul. 1999).

Scheuner, D., et al., "Secreted amyloid β-protein similar to that in the senile plaques of Alzheimer's disease is increased *in vivo* by the presenilin 1 and 2 and APP mutations linked to familial Alzheimer's disease," *Nat. Med.* 2:864-870, Nature Publishing Co. (1996).

Seiler, C., and Nicolson, T., "Defective Calmodulin-Dependent Rapid Apical Endocytosis in Zebrafish Sensory Hair Cell Mutants," *J. Neurobiol.* 41:424-434, John Wiley & Sons (Nov. 1999).

Selkoe, D.J., "Cell Biology of the Amyloid β-Protein Precursor and the Mechanism of Alzheimer's Disease," *Annu. Rev. Cell. Biol.* 10:373-403, Annual Reviews Inc. (1994).

Selkoe, D.J., "Imaging Alzheimer's amyloid," *Nat. Biotechnol.* 18:823-824, Nature America (Aug. 2000).

Shoji, M., et al., "Production of the Alzheimer Amyloid β Protein by Normal Proteolytic Processing," *Science* 258:126-129, American Association for the Advancement of Science (1992).

Steiner, H., et al., "Genes and mechanisms involved in β-amyloid generation and Alzheimer's disease," *Eur. Arch. Psychiatry Clin. Neurosci.* 249:266-270, Springer-Verlag (Dec. 1999).

Stoppini, L., et al., "A simple method for organotypic cultures of nervous tissue," *J. Neurosci. Meth. 37*:173-182, Elsevier Science B.V. (1991).

Strimmatter, W.J., et al., "Hypothesis: Microtubule Instability and Paired Helical Filament Formation in the Alzheimer Disease Brain Are Related to Apolipoprotein E Genotype," *Exp. Neurol. 125*:163-171, Academic Press (1994).

Sturchler-Pierrat, C., and Sommer, B., "Transgenic Animals in Alzheimer's Disease Research," *Rev. Neurosci. 10*:15-24, Freund & Pettman (Jan. 1999).

Suzuki, N., et al., "An Increased Percentage of Long Amyloid β Protein Secreted by Familial Amyloid β Protein Precursor (βAPP$_{717}$) Mutants," *Science 264*:1336-1340, American Association for the Advancement of Science (1994).

Torimoto, Y., et al., "A Monoclonal Antibody (8H3) that Binds to Rat T Lineage Cells and Augments In Vitro Proliferative Responses," *J. Exp. Med. 172*:1315-1323, The Rockefeller University Press (1990).

Tsao, P.W., and Mousa, S.A., "Thrombospondin Mediates Calcium Mobilization in Fibroblasts via Its Arg-Gly-Asp and Carboxyl-terminal Domains," J. Biol. Chem. 270:23747-23753, The American Society for Biochemistry and Molecular Biology (1995).

van Leuven, F., "Single and multiple transgenic mice as models for Alzheimer's disease," *Prog. Neurobiol. 61*:305-312, Elsevier Science (Jun. 2000).

Vekrellis, K., et al., "Neurons Regulate Extracellular Levels of Amyloid β-Protein via Proteolysis by Insulin-Degrading Enzyme," *J. Neurosci. 20*:1657-1665, Society for Neuroscience (Mar. 2000).

Vigo-Pelfrey, C., et al., "Characterization of β-Amyloid Peptide from Human Cerebrospinal Fluid," *J. Neurochem. 61*:1965-1968, Raven Press (1993).

Vincent, I., et al., "Mitotic Phosphoepitopes Precede Paired Helical Filaments in Alzheimer's Disease," *Neurobiol. Aging 19*:287-296, Elsevier Science (1998).

Walsh, D.M., et al., "The Oligomerization of Amyloid β-Protein Begins Intracellularly in Cells Derived from Human Brain," *Biochemistry 39*:10831-10839, American Chemical Society (Published on the Web, Aug. 2000).

Ward, E.S., et al., "Binding activities of a repertoire of single immunoglobulin variable domains secreted from *Escherichia coli*," *Nature 341*:544-546, Macmillan Magazines (1989).

Woods, A.G., et al., "Dexamethasone Selectively Suppresses Microglial Trophic Responses to Hippocampal Deafferentation, ," *Neurosci. 91*:1277-1289, Elsevier Science (Jul. 1999).

Wu, X., et al., "Modulation of Calcium Current in Arteriolar Smooth Muscle by $\alpha_v\beta_3$ and $\alpha_5\beta_1$ Integrin Ligands," *J. Cell Biol. 143*:241-252, The Rockefeller University Press (1998).

Yamazaki, T., et al., "Cell Surface Amyloid β-Protein Precursor Colocalizes with β1 Integrins at Substrate Contact Sites in Neural Cells," *J. Neurosci. 17*:1004-1010, Society for Neuroscience (1997).

Yang, A.J., et al., "Loss of Endosomal/Lysosomal Membrane Impermeability Is an Early Event in Amyloid Aβ1-42 Pathogenesis," *J. Neurosci. Res. 52*:691-698, Wiley-Liss (1998).

\* cited by examiner

SEQUENCE LISTING

```
<160> NUMBER OF SEQ ID NOS: 5

<210> SEQ ID NO 1
<211> LENGTH: 4
<212> TYPE: PRT
<213> ORGANISM: Unknown
<220> FEATURE:
<223> OTHER INFORMATION: Synthetic Peptide

<400> SEQUENCE: 1

Arg Gly Asp Ser
1

<210> SEQ ID NO 2
<211> LENGTH: 5
<212> TYPE: PRT
<213> ORGANISM: Unknown
<220> FEATURE:
<223> OTHER INFORMATION: Synthetic Peptide

<400> SEQUENCE: 2

Gly Arg Gly Asp Ser
1               5

<210> SEQ ID NO 3
<211> LENGTH: 6
<212> TYPE: PRT
<213> ORGANISM: Unknown
<220> FEATURE:
<223> OTHER INFORMATION: Synthetic Peptide

<400> SEQUENCE: 3

Gly Arg Gly Asp Ser Pro
1               5

<210> SEQ ID NO 4
<211> LENGTH: 6
<212> TYPE: PRT
<213> ORGANISM: Unknown
<220> FEATURE:
<223> OTHER INFORMATION: Synthetic Peptide

<400> SEQUENCE: 4

Gly Arg Gly Asp Thr Pro
1               5

<210> SEQ ID NO 5
<211> LENGTH: 6
<212> TYPE: PRT
<213> ORGANISM: Unknown
<220> FEATURE:
<223> OTHER INFORMATION: Synthetic Peptide

<400> SEQUENCE: 5

Gly Arg Ala Asp Ser Pro
1               5
```

DETERMINING THE EFFECT OF A SUBSTANCE ON SEQUESTRATION, UPTAKE, AND ACCUMULATION OF AMYLOID IN BRAIN CELLS

CROSS-REFERENCES TO RELATED APPLICATIONS

This application claims the benefit of U.S. Provisional Application No. 60/235,374 filed Sep. 25, 2000, the contents of which is incorporated herein by reference in its entirety.

STATEMENT AS TO RIGHTS TO INVENTIONS MADE UNDER FEDERALLY SPONSORED RESEARCH AND DEVELOPMENT

This invention was made with Government support under Grant No. 455365-30110, awarded by the National Institute of Aging. The Government may have certain rights in this invention

FIELD OF THE INVENTION

The invention is in the field of models and interventions of medical diseases. Specifically, the invention is in the field of neurodegenerative disease models and treatments, and especially age related neurodegenerative diseases such as Alzheimer's disease.

BACKGROUND OF THE INVENTION

Alzheimer's disease (AD) is a leading cause of dementia in the elderly, affecting 5–10% of the population over the age of 65 years. See *A Guide to Understanding Alzheimer's Disease and Related Disorders*, edited by Jorm, New York University Press, New York (1987). AD currently affects 12 million people around the world, and is projected to affect 22 million people by 2025 and 45 million by 2050.

Alzheimer's disease is histopathologically characterized by the loss of particular groups of neurons and the appearance of two principal lesions within the brain, termed senile plaques and neurofibrillary tangles. See Brion et al., *J. Neurochem.* 60:1372–1382 (1993). Neurofibrillary tangles are intraneuronal accumulations of an abnormally phosphorylated form of the microtubule protein tau. Neurofibrillary tangles are most abundantly present in parts of the brain associated with memory functions, such as the hippocampus and adjacent parts of the temporal lobe. See *Robbins Pathologic Basis of Disease*, Cotran et al., 6th ed., W. B. Saunders Company (1999), p. 1300.

Amyloid beta peptides (Aβ) are normally secreted proteolytic products of amyloid precursor protein (APP) (Selkoe, D. J., *Annu Rev Cell Biol* 10:373–403 (1994)). The 42-residue form (Aβ1–42) is the principal species in senile plaques which constitute a diagnostic feature of Alzheimer's disease (AD), and is preferentially generated over shorter forms (e.g., Aβ1–40) in genetic mutations related to familial AD (Steiner, H., et al., *Eur Arch Psychiatry Clin Neurosci* 249:266–270 (1999)). Transgenic mice that overexpress mutant APP develop plaques accompanied by neuropathology (Guenette, S. Y., and Tanzi, R. E., *Neurobiol Aging* 20:201–11 (1999); van Leuven, 2000) with both effects being blocked by immunization against Aβ (Schenk, D., et al., *Nature* 400:173–177 (1999); Frenkel, D., et al., *Proc Natl Acad Sci USA* 97:11455–11459 (2000); Janus, C., et al., *Biochim Biophys Acta* 1502:63–75 (2000); Morgan, D., et al., *Nature* 408:982–85 (2000)), or by peripheral administration of antibodies against Aβ (Bard, F., et al., *Nat Med* 6:916–9 (2000)).

These results support the assumption that extracellular Aβ accumulations trigger pathologies and emphasize the importance of identifying links between the peptide and pathogenic processes. Infusions of Aβ into brain do not cause extensive damage (Games, D., et al., *Neurobiol Aging* 13:569–576 (1992); Podlisny, M. B., et al., *Am J Pathol* 142:17–24 (1993)), in part, because extracellular proteases prevent the injected material from assembling into plaques (Backstrom, J. R., et al., *J Neurosci* 16:7910–7919 (1996); Qiu, W. Q., et al., *J Biol Chem* 273:32730–32738 (1998); Caswell, M. D., et al., *Eur J Biochem* 266:509–516 (1999); Iwata, N., et al., *Nature Med* 6:143–150 (2000); Vekrellis, K., et al., *J Neurosci* 20:1657–1665 (2000)). In any event, links between extracellular Aβ and pathogenic mechanisms in mature brain remain obscure.

Brain slices in interface culture reach a surprisingly adult-like state (Stoppini, L., et al., *J Neurosci Meth* 37:173–182 (1991); Muller, D., et al., *Dev Brain Res* 71:93–100 (1993); Bahr, B. A., et al., *Hippocampus* 5:425–439 (1995)) and offer opportunities for in vitro studies of brain aging. Initial studies using this model found that Aβ treatment moderately enhanced cell death (Bruce, A., et al., *Proc Nat Acad Sci* 93:2312–2316 (1996)), while a later study found little effect of Aβ1–42 on measures of pathogenesis (Bahr, B., et al., *J Comp Neuro* 397:139–147 (1998)). A third study confirmed that Aβ alone did not cause pathology but in combination with transforming growth factor-β induced neuronal degeneration in field CA1 (Harris-White, M. E., et al., *J Neurosci* 18:10366–10374 (1998)).

The relatively weak effects of Aβ on cultured slices could reflect slow internalization and modest accumulation. Uptake of Aβ1–42 in cultured hippocampal slices occurs selectively in field CA1 (Bahr, B., et al., *J Comp Neurol* 397:139–147 (1998); Harris-White, M. E., et al., *J Neurosci* 18:10366–10374 (1998)), suggesting the existence of regionally differentiated factors that govern sequestration and regulate toxicity of the peptide. Integrins mediate internalization of bacteria and viruses (Isberg, R. R., and Tran Van Nhieu, G., *Trends Microbiol* 2:10–14 (1994); Nemerow, G. R., and Stewart, P. L., *Microbiol Mol Biol Rev* 63:725–734 (1999)) and bind Aβ via an Arg-Gly-Asp (RGD)-like sequence (Ghiso, J., et al., *Biochem J* 288:1053–1059 (1992); Sabo, S., et al., *Neurosci Lett* 184:25–28 (1995); Yamazaki, T., et al., *J Neurosci* 17:1004–1010 (1997)). Binding to alpha5β1 integrin, a fibronectin receptor densely expressed in hippocampus (Bahr, B., et al., *Neuroreport* 2:13–16 (1991); Bahr, B. and Lynch, G., Biochem J 281:137–142 (1992); Pinkstaff, J. K., et al., *J Neurosci* 19:1541–1556 (1999); Bi, X., et al., *J Comp Neurol* 435:184–193 (2001)) is required for Aβ internalization in cell lines (Matter, M. L., et al., *J Cell Biol* 141:1019–1030 (1998)). Moreover, the different subdivisions of hippocampus express different combinations of integrins (Pinkstaff, J. K., et al., *J Neurosci* 19:1541–1556 (1999)), an anatomical feature that could account for regional variations in Aβ uptake.

Integrins interact with neighboring transmembrane proteins to produce their effects on cell surface operations (Burkin, D. J., et al., *J Cell Biol* 143:1067–1075 (1998); Porter, J. C., and Hogg, N., *Trends Cell Biol.* 8:390–396 (1998)) including calcium influx (Tsao, P. W., and Mousa, S. A., *J Biol Chem* 270:23742–23753 (1995); Wu, X., et al., *J Cell Biol* 143:241–252 (1998)). NMDA receptors are calcium permeant, coupled to the actin cytoskeleton (Dunah, A.

W., et al., *Brain Res Mol Brain Res* 79:77–87 (2000)); both calcium (Marsh, M., and McMahon, H. T., *Science* 285: 215–220 (1999)) and the actin network (Gottlieb, T. A., et al., *J Cell Biol* 120:695–710 (1993)) are crucial to endocytosis. NMDA receptor function (Bahr, B. A., *J Neurosci Res* 59:827–832 (2000)) and maturation of synapses containing NMDA receptors (Chavis, P., and Westbrook, G., *Nature* 411:317–321 (2001)) have been shown to be modulated by integrins. Finally, recent studies indicate that NNMDA receptor activation can trigger clathrin-mediated internalization (Carroll, R. C., *Proc Natl Acad Sci USA* 96:14112–14117 (1999); Beattie, E. C., et al., *Nat Neurosci* 3:1291–300 (2000); Ehlers, M. D., *Neuron* 28:511–25 (2000)).

There has been considerable research into mechanisms underlying neurodegenerative diseases, including Alzheimer's disease. For example, many transgenic animal models of Alzheimer's disease have been developed and used in an attempt to study the mechanisms of Alzheimer's disease as well as to screen compounds that may ameliorate the conditions of Alzheimer's disease. However, many in vivo or in vitro models are unable to produce some of the important features of Alzheimer's disease, such as neurofibrillary tangles, microglia activation, lysosomal dysfunction, intracellular and/or extracellular sequestration and/or uptake and/or accumulations of amyloid, etc. Thus, there is an ongoing need to develop a model that better mimics the pathologies associated with neurodegenerative diseases including Alzheimer's disease and new ways to investigate and combat such conditions.

The present invention provides a model that better mimics some of the pathologies of neurodegenerative diseases, including Alzheimer's disease, than other models known in the art. The present invention meets these and other needs, and also provides new ways to investigate and combat such neurodegenerative conditions. Related to the present invention is U.S. application Ser. No. 09/917,789 which is incorporated by reference herein in its entirety

SUMMARY OF THE INVENTION

The present invention provides a model for neurodegenerative diseases, including Alzheimer's disease and other age-related neurodegenerative diseases, wherein the model provides brain cells, or brain tissue containing the same. The invention further provides a method for increasing or decreasing characteristics and changes indicative of neurodegenerative diseases in such cells. These changes especially include increasing sequestration of and/or accumulation of and/or uptake of A$\beta$, and/or lysosomal dysfunction, and/or microglia activation. The present invention also provides a model wherein brain cells comprise a marked microglia activation and increases in the levels and/or activity of cathepsin D. As described above, many currently available in vivo and in vitro models of neurodegenerative diseases and aged brain lack some or all of these key features.

The present invention is based on, in part, the discovery that integrins and/or integrin receptors can modulate the sequestration and/or accumulation and/or uptake of A$\beta$ in cultured brain cells. Further, the present invention is also based upon the discovery that glutamate receptors within the brain, for example the NMDA-subtype of glutamate receptors, can modulate the sequestration and/or accumulation and/or uptake of A$\beta$ in cultured brain cells. Specifically, the treatment of brain cells with agent(s) capable of modulating integrins and/or integrin receptors surprisingly triggered the sequestration and/or accumulation and/or uptake of A$\beta$. Further, agent(s) which affect glutamate receptors within the brain, for example the NMDA-subtype of glutamate receptors, blocked the modulation of the sequestration and/or accumulation and/or uptake of A$\beta$ in brain cells treated with agent(s) capable of modulating integrins and/or integrin receptors. These results can be observed in any suitable brain cells including, e.g., normal brain cells, brain cells derived from transgenic animals, etc.

Among many types of brain cells suitable for embodiments of the invention, hippocampal brain cells treated with agent(s) capable of modulating integrins and/or integrin receptors produced sequestration and/or accumulations and/or uptake of A$\beta$ at significantly enhanced levels when compared with hippocampal brain cells not treated with agent(s) capable of modulating integrins and/or integrin receptors. The enhanced sequestration and/or accumulations and/or uptake of A$\beta$ are typically formed within a few days of treatment, and morphologically mimic early stage amyloid sequestration and/or accumulations and/or uptake found in the brains of Alzheimer's patients. Such levels of sequestration and/or accumulations and/or uptake of A$\beta$ was not achievable in brain cells in vitro even with prolonged treatment with A$\beta$ without the presence of agent(s) capable of modulating integrins and/or integrin receptors. Therefore, if brain cells with robust sequestration and/or accumulations and/or uptake of A$\beta$ is desired, the use of agent(s) capable of modulating integrins and/or integrin receptors can be preferably used in embodiments of the invention. Thus, the present invention provides, among other things, brain cells in vitro comprising enhanced levels of sequestration and/or accumulations and/or uptake of A$\beta$ which can be used as a model for neurodegenerative diseases, including Alzheimer's disease.

Accordingly, in one aspect, the invention provides an in vitro method of increasing sequestration and/or accumulation and/or uptake of A$\beta$, the method comprising: (a) contacting cultured brain cells with agent(s) capable of modulating integrins and/or integrin receptors; and (b) determining the sequestration of and/or accumulation of and/or uptake of A$\beta$ in the cell culture.

In another aspect, the invention provides a method comprising, contacting brain cells with a compound that is capable of modulating integrins and/or integrin receptors, thereby producing properties of a brain afflicted with a neurodegenerative disease, wherein the properties include increased sequestration of and/or accumulation of and/or uptake of A$\beta$.

In yet another aspect, the invention provides brain cells in vitro that have been cultured in a medium capable of modulating integrins and/or integrin receptors in the brain cells, wherein the brain cells comprise an increased amount of sequestration of and/or accumulation of and/or uptake of A$\beta$ compared to a control.

In yet another aspect, the invention provides brain cells in vitro, wherein the brain cells have been treated with a compound that is capable of modulating integrins and/or integrin receptors, thereby producing properties of a brain afflicted with a neurodegenerative disease, wherein the properties include increased sequestration of and/or accumulation of and/or uptake of A$\beta$.

In yet another aspect, the invention provides a screening method comprising: (a) contacting brain cells in vitro, with a compound that is capable of modulating integrins and/or integrin receptors in the brain cells, wherein the compound is capable of increasing the sequestration of and/or accumulation of and/or uptake of A$\beta$; (b) contacting the brain cells with an agent; and (c) determining whether the agent modulates the amount of sequestration of and/or accumulation of and/or uptake of Aβ in the brain cells treated with the agent compared to the brain cells that are not treated with the agent.

In yet another aspect, the invention provides a method of increasing the sequestration of and/or accumulation of and/or uptake of Aβ in any suitable brain cells, the method comprising: (a) contacting the brain cells in a medium which is capable of modulating integrins and/or integrin receptors; and (b) determining the sequestration of and/or accumulation of and/or uptake of Aβ in the brain cells.

In another aspect, the invention provides a method comprising: (a) culturing brain cells; and (b) contacting the brain cells with a compound which is capable of modulating integrins and/or integrin receptors, thereby producing properties of a brain afflicted with a neurodegenerative disease, wherein the properties include increased sequestration of and/or accumulation of and/or uptake of Aβ.

In yet another aspect, the invention provides brain cells in vitro that have been cultured in a medium which modulates integrins and/or integrin receptors in the brain cells, wherein the brain cells comprise an increased sequestration of and/or accumulation of and/or uptake of Aβ compared to a control.

In yet another aspect, the invention provides brain cells in vitro, wherein the brain cells have been treated with a compound that modulates integrins and/or integrin receptors in the brain cells, thereby producing properties of a brain afflicted with a neurodegenerative disease, wherein the properties include increased sequestration of and/or accumulation of and/or uptake of Aβ.

In yet another aspect, the invention provides a screening method comprising: (a) contacting brain cells in vitro, with a compound that modulates integrins and/or integrin receptors in the brain cells, wherein the modulation of integrins and/or integrin receptors is capable of increasing the sequestration of and/or accumulation of and/or uptake of Aβ in the brain cells; (b) contacting the brain cells with an agent; and (c) determining whether the agent modulates the amount of sequestration of and/or accumulation of and/or uptake of Aβ in the brain cells treated with the agent compared to the brain cells that are not treated with the agent.

In yet another aspect, the invention provides a method for determining the effect of a substance on characteristics of neurodegenerative disease in brain cells, said method comprising: (A) exposing brain cells to a condition that modulates integrins or integrin receptors in said cells, (B) maintaining said cells for a time sufficient to induce one or more characteristics of a neurodegenerative disease in said cells, (C) adding said substance before, during and/or after said exposing or maintaining; and (D) determining whether the presence of said substance has an effect on one or more of said characteristics.

Another aspect of the invention provides method of obtaining brain cells having characteristics of neurodegenerative disease comprising (A) culturing brain cells, (B) exposing said brain cells to a condition that modulates integrins or integrin receptors in said cells, and (C) maintaining said cells or brain tissue for a time sufficient to induce one or more characteristics of a neurodegenerative disease in said cells.

Another aspect of the invention is directed to an in vitro method for increasing at least one or more characteristics of neurodegenerative disease in brain cells, wherein said characteristics are selected from the group consisting sequestration of Aβ, accumulation of Aβ, uptake of Aβ, lysosomal dysfunction and microglia activation, said in vitro method comprising:

(A) exposing brain cells in culture to a condition that modulates integrins or integrin receptors in said cells wherein said modulation results in increase in characteristics of neurodegenerative disease in said cells, and (B) maintaining said cells in culture for a time sufficient to increase one or more characteristics of a neurodegenerative disease in said cells.

Another aspect of the invention is directed to a method for determining the effect of a substance on inhibition of characteristics of neurodegenerative disease in brain cells, said method comprising: (A) exposing brain cells to a condition that modulates integrins or integrin receptors in said cells, (B) maintaining said cells for a time sufficient to induce one or more characteristics of a neurodegenerative disease in said cells, (C) adding said substance before, during and/or after said exposing or maintaining; and (D) determining whether the presence of said substance inhibits one or more of said characteristics.

The invention is also directed to a method for determining the effect of a substance on inhibition of characteristics of neurodegenerative disease in brain cells, said method comprising: (A) exposing brain cells to a condition that modulates integrins or integrin receptors in said cells, (B) maintaining said cells for a time sufficient to induce one or more characteristics of a neurodegenerative disease in said cells, (C) adding said substance before, during and/or after said exposing or maintaining; and (D) determining whether the presence of said substance inhibits one or more of said characteristics.

Aspects of the invention include methods drawn to the effect of the substance on characteristics selected from the group consisting of sequestration of Aβ, accumulation of Aβ, uptake of Aβ and lysosomal dysfunction, changes in cathepsin D content and microglia activation. Additional embodiments look at increases or decreases of these characteristics, such as where the changes are at least about 10% compared to a control.

The methods of the invention are also drawn to obtaining brain cells and the use of brains cells wherein the brain cells may be in vivo or in vitro such as in the form of a brain slice. The brain slice may include a hippocampal slice, an entorhinal cortex slice, an entorhinohippocampal slice, a neocortex slice, a hypothalamic slice, or a cortex slice. Brain cells may also be obtained from a non-human transgenic animal. Such animals may comprise a human apolipoprotein E4 gene or and animal where an endogenous apolipoprotein E gene of the non-human transgenic animal are ablated. Apolipoprotein E deficient brain cells or apolipoprotein E4 containing brain cells cultured in a medium which selectively increases are also included in the invention.

The methods of the invention are also drawn to culturing brain slices or the cells therein in a medium that comprises an antagonist or modulator of an integrin. The modulator or antagonist may be selected from the group consisting of neutralizing and/or function blocking antibodies for integrin subunits alpha1, alpha2, alpha3, alpha4, alpha5, alpha6, alpha7, alpha8, beta1, beta2, beta3, beta4, beta5, beta6, beta7 and beta8. The methods of the invention are further drawn to a peptide selected from the group of peptides consisting of RGD, RGDS (SEQ. ID NO.1), GRGDS (SEQ. ID NO.2), GRGDSP (SEQ. ID NO.3), GRGDTP (SEQ. ID NO.4), mimetics thereof and disintegrins such as echistatin found in snake venom.

The methods of the invention are also directed to determining visually the amount of: sequestration of Aβ, accumulation of Aβ, uptake of Aβ, lysosomal dysfunction or microglia activation is determined visually. The determinations may be done visually and also using a capture reagent. The capture reagents may include is an antibody that binds to Aβ, lysosomes, cathepsin D or a microglia element.

The methods of the invention are also directed to either contacting the brain cells simultaneously with the compound that modulates integrins and/or integrin receptors or contacting the brains cells with the compound that modulates integrins and/or integrin receptors prior to contact with the substance whose effect is being determined.

Another aspect of the invention is directed to a method for alleviating the symptoms of disease states having at least one of the following characteristics selected from the group consisting of intracellular uptake of amyloid protein, amyloid accumulation and/or plaque formation, said method comprising: (A) administering to a patient in need thereof a composition comprising an effective amount of an NMDA receptor antagonist, and (B) determining the effectiveness of treatment with said composition, (C) increasing or decreasing the composition based on the determinative testing, and (D) alleviating symptoms of the disease. Determinative testing may include methods of brain imaging such as MRI or PET. Additional, determinative testing may include electroencephalogram analysis as well as cognitive testing.

The invention is also directed to a pharmaceutical composition comprising a compound capable of sufficiently inhibiting the activity of the NMDA receptors in an amount effective to alleviate one or more symptoms of disease states associated with at least one characteristic selected from the group consisting of abnormal accumulation, abnormal molecular organization of amyloid protein and/or amyloid plaques and said composition also includes a suitable carrier or pharmaceutical excipient. Embodiments of the invention may include a composition comprising at least one of the compounds selected from a group consisting of magnesium, ketamine, dextromethorphan, amantadine, dexanabinol, AP3, AP5, AP6, AP7, 4C3HPG, 4CPG, CGS 19755, chlorophenylglutamic acid, CPP, MK-801, PCP, ibogaine, noribogaine, ifenprodil, fiupirtine, selfotel, D-CPP-ene, procyclidine, trihexyphenidyl, CP-101606, CP-98113, GVI150526, AR-R15896AR, NPS 1506, NPC 12626, LY274614, LY 2835959, SDZ 220-040, SDZ 220-040, SDZ 220-581, SDZ 221-653 and memantine.

Another aspect of the invention is directed to a method for inhibiting the intracellular accumulation of amyloid comprising: (A) contacting brain cells with a glutamate receptor antagonist and (B) determining whether the intracellular accumulation of amyloid is inhibited.

BRIEF DESCRIPTION OF THE DRAWINGS

FIG. 1A. Low magnification photomicrograph of a hippocampal explant showing Aβ1–42 immunostaining is restricted to a subpopulation of cells in CA1 stratum pyramidale (bracketed by arrows; DG, dentate gyrus).

FIG. 1B. Higher magnification photomicrograph of the field of immunostaining shows that Aβ-ir is localized within small puncta in stratum pyramidale (sp) and, very faintly, within dendritic processes in stratum radiatum (sr) (so, stratum oriens). The scale bar used in FIG. 1B=0.5 mm for FIG. 1A and 50 μm for FIG. 1B.

FIG. 2A Low magnification photomicrograph of a cultured slice showing a broad, dense field of Aβ-ir neurons which is confined to stratum pyramidale of fields CA1 and CA2, and the relatively greater incorporation in this case as compared to the representative slice treated with Aβ1–42 alone, shown in FIG. 1A.

FIG. 2B. Higher magnification image of CA1 stratum pyramidale showing incorporated Aβ-ir ("ir"=immunoreactive) is limited to neuronal cell bodies and proximal dendrites. Dark perinuclear cytoplasmic staining is evident.

FIG. 2C. High magnification photomicrograph of neurons in field CA1c showing Aβ-ir is localized to puncta tightly clustered around the nucleus but also scattered into proximal apical and basal dendrites. Diffuse staining of the dendritic processes is also evident.

FIG. 2D. Photomicrograph of Aβ immunostaining at the border between CA1 (left side) and CA2 (right side) stratum pyramidale of a slice treated with Aβ1–42 and GRGDSP (SEQ. ID. No.3) showing subfield differences in the compartmentalization of sequestered amyloid peptide: relatively homogenous cytoplasmic immunostaining predominates in field CA2 while CA1 pyramidal cells exhibit both diffuse cytoplasmic and dense perinuclear aggregates of Aβ-ir. The scale bar used in FIG. 2A=0.5 mm; 50 μm in FIG. 2B; 24 μm in FIG. 4C–4D.

Digitized images of Aβ-ir (black) in field CA1b in sections through cultured hippocampal slices incubated with Aβ1–42 alone (FIG. 4A) or in the presence of GRADSP (SEQ. ID. No.5) (FIG. 4B), echistatin (FIG. 4C), or GRGDSP (SEQ. ID. No.3) (FIG. 4D). Stained elements at or above a specified and consistent density threshold were selected as "positive particles" and highlighted in black using the "density slice" function of NIH Image software as described in Methods. Graphs in FIGS. 4E–4G show the mean area of selected Aβ-ir particles (FIG. 4E), the total area of Aβ-ir particles (FIG. 4F), and the number of Aβ-ir particles (FIG. 4G) within the sample field for slices treated with Aβ1–42 alone (Aβ), Aβ1–42 plus GRADSP (SEQ. ID. No.5) (RAD/Aβ), Aβ1–42 plus echistatin (Echi/Aβ) and Aβ1–42 plus GRGDSP (SEQ. ID. No.3) (RGD/Aβ). Values shown in FIG. 4E–4G are group means±sem, expressed as a percent of values obtained in slices treated with Aβ alone; the "n" for each group is indicated in white on each bar. *p<0.05; **p<0.01; 2-tail t-test for comparison to Aβ-alone values. The scale bar used in FIG. 4A=50 μm for to FIG. 4A–4D.

Figure 5:
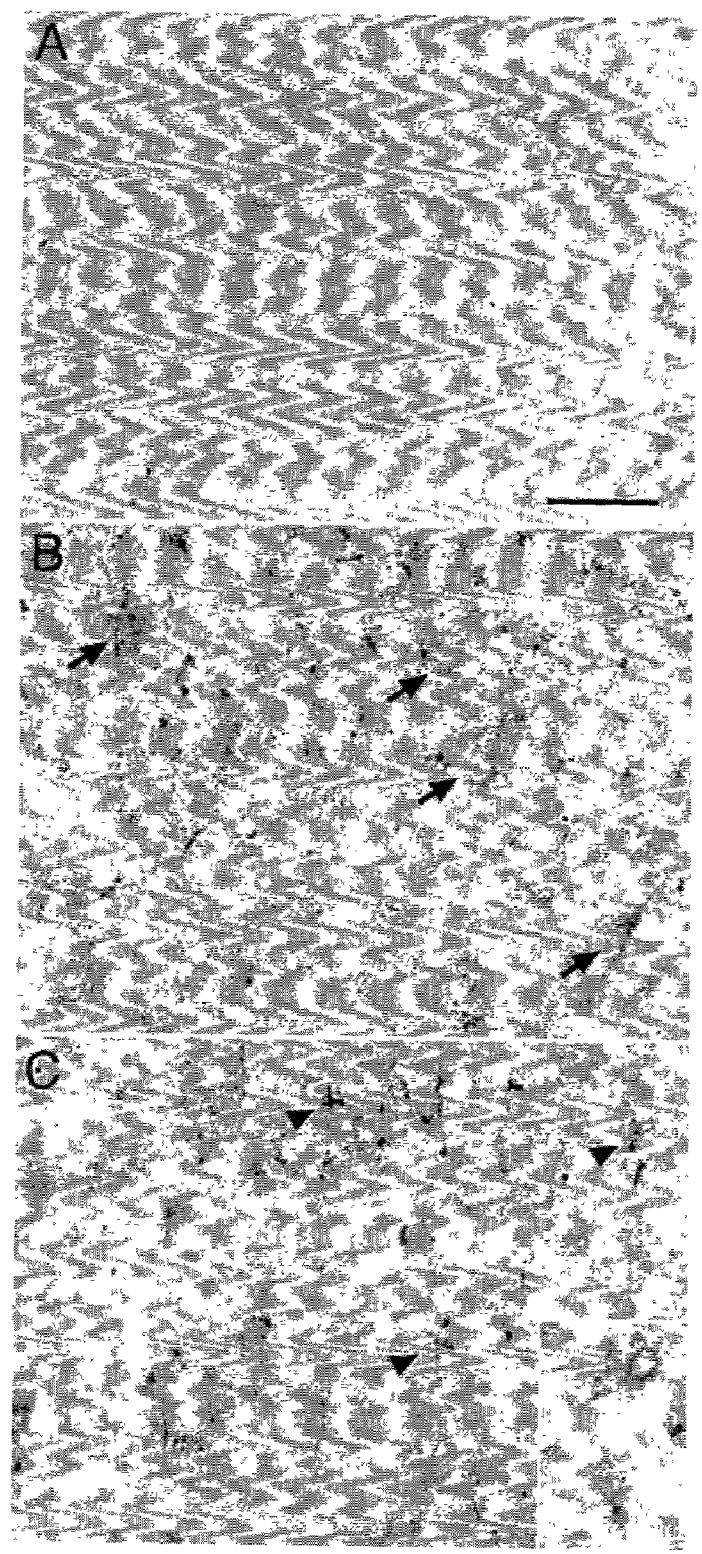

FIG. 5A–5C. Integrin antagonism potentiates amyloid effects on cathepsin D content. Hippocampal slices were cultured for 12 days followed by 6 days incubation with (FIG. 5A) Aβ1–42 alone or (FIG. 5B–5C) Aβ1–42 plus GRGDSP (SEQ. ID. No.3) and then processed for the immunocytochemical localization of cathepsin D. Panels show CA1 stratum pyramidale. In tissue with the combined treatment (FIG. 5B–5C) cathepsin B-ir is elevated and present in coarser puncta as compared to staining in tissue exposed to Aβ1–42 alone (FIG. 5A). Arrows in B indicate some neurons with cytoplasmic immunostaining and coarse immunoreactive inclusions. Arrowheads in FIG. 5C indicate cathepsin D-ir deposits within probable microglial cells. Insert in FIG. 5C shows intraneuronal cathepsin D-ir puncta that exhibit lysosome-like distributions. The scale bar used in FIG. 5A=50 μm for FIG. 5A–5C.

FIG. 6A–6D. Co-distribution of neuronal Aβ incorporation and reactive microglia. Photomicrographs of tissue from a hippocampal explant treated with Aβ1–42 and 2 mM GRGDSP (SEQ. ID. No.3) for 6 days and processed for the simultaneous immunocytochemical localization of sequestered Aβ (dark gray) and ED-1 reactive microglia (black). (FIG. 6A) Low magnification photomicrograph showing that both Aβ-ir and ED-1-ir are clustered in stratum pyramidale of CA1 and CA3c extending into the hilus (H); both markers are low in the extra-hilar postion of CA3 and stratum granulosum. (FIG. 6B–6C) Higher magnification photomicrographs show details of co-distributed immunoreactivities within CA1b (FIG. 6B) and CA3c (FIG. 6C), two regions where Aβ uptake is most frequently encountered. (FIG. 6D) Photomicrograph of field CA2 showing the presence of ED-1 positive microglia within a field of Aβ-ir (right side of panel) and the lack of reactive microglia in an immediately adjacent field lacking Aβ-ir neurons (left side of panel). The scale bar used in FIG. 6D=0.5 mm for FIG. 6A; 50 μm for For FIG. 6B; 80 μm for FIG. 6C and FIG. 6D. re co-localized.

Figure 7:
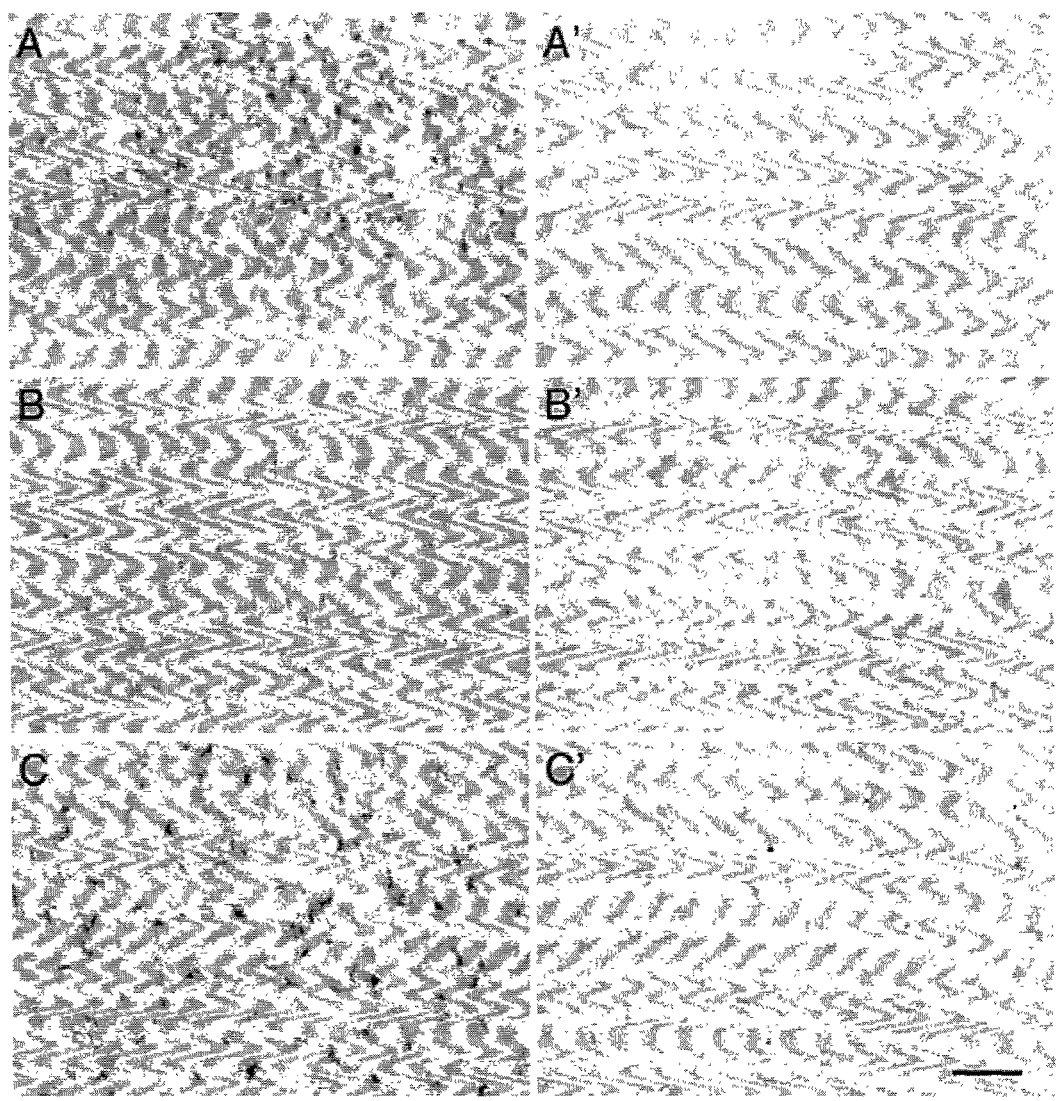

FIG. 7. GRGDSP-enhancement (SEQ. ID. No.3) of Aβ uptake, cathepsin D-ir increases and microglial activation are all blocked by NMDA receptor antagonists. GRGDSP-enhancement (SEQ. ID. No.3)of Aβ uptake, cathepsin D-ir and microglial activation is blocked by the NMDA receptor antagonist AP5. Cultured hippocampal slices were treated with Aβ1–42 and 2 mM GRGDSP (SEQ. ID. No.3) only (A,B,C) or in the presence of 50 μM AP5 (A', B', C') for 6 days and processed for the localization of Aβ1–42 (A,A'), cathepsin D (B,B'), or ED-1 (C,C') immunoreactivities. As shown, AP5 completely eliminated Aβ uptake (A') and suppressed cathepsin D-ir (B') and ED-1-ir (C') to vehicle control levels. The scale bar used in FIG. 7C'=50 μm for all panels.

DEFINITIONS

As used herein, the following terms have the meanings ascribed to them unless specified otherwise.

The terms "A-beta" and "Aβ" refer to a peptide, also referred to as "amyloid beta peptide", or "amyloid", that is typically about 39–42 amino acids in length. Aβ is a normally secreted proteolytic product of the carboxyterminal domain of the amyloid protein precursor (APP) (Busciglio, J. et al., *Proc. Natl. Acad. Sci. USA* 90:2092–2096 (1993), Haass, C et al., *Nature* 357:500–503 (1992), Shoji et al., *Science* 258:126–129 (1992)). The 42 residue form (Aβ1–42) is generally agreed to be the principal species in the senile plaques which constitute a diagnostic feature of Alzheimer's disease (AD) (Kang, J. et al., *Nature* 325: 733–736 (1987), Miller, D. L. et al., *Arch. Biochem. Biophys.* 301:41–52 (1993)) and is preferentially generated over shorter forms (Aβ1–40) in genetic mutations related to familial AD (Haas, C. et al., *J. Biol. Chem.* 269:17741–17748 (1994), Vigo, P. et al., *J. Neurochem* 61:1965–1968 (1993), Vincent, I. et al., *Neurobiol. Aging* 19:287–296 (1998)). Transgenic mice that overexpress mutant APP gradually develop plaques accompanied by neuropathology (see Sturchler, P. et al., *Rev. Neurosci.* 10: 15–24 (1999)) with both effects being blocked by immunization against Aβ (Motter, R. et al., *Nature* 400:173–177 (1999). The terms "A-beta" and "Aβ" are generically used to refer to an amino acid length from 1–42 amino acids derived from, or modeled after, the APP protein, and also the terms can refer to any homologs from human, rat, mouse, rabbit, guinea pig, etc., and their variants.

The term "activation" when used to refer to microglia may refer to a transformation of the microglia, for example, from a silent/quiet (slim cell body with ramified thin process) state to an active/macrophage-like (rounded cell body without process) state. Additionally, the term may refer to an enhanced ability to express and secrete cytokines.

"Alzheimer's disease" refers to a condition associated with: 1) the formation of neuritic plaques comprising amyloid beta protein and neurofibrillary tangles comprising tau proteins (primarily located in the hippocampus and cerebral cortex) and, 2) an impairment in both learning and memory. "Alzheimer's disease" as used herein includes all kinds of Alzheimer's disease, including, e.g., early onset family type Alzheimer's disease and late onset sporadic Alzheimer's disease.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group. Examples of amino acid analogs include homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but functions in a manner similar to a naturally occurring amino acid.

Amino acids may be referred to herein by either their commonly known three letter symbols or by the one-letter symbols recommended by the IUPAC-IUB Biochemical Nomenclature Commission.

The terms "Apolipoprotein E" and "apoE" refers to a protein that is about 299 amino acids in length and has a molecular weight of about 34,000 Daltons, and plays a major role in lipid transport and metabolism. Specifically, apoE functions as a cholesterol transport protein within the periphery. ApoE is produced in abundance in brain and apoE-containing lipoproteins are the principal lipoproteins in the Cerebro-Spinal Fluid (CSF). In the periphery, apoE expression is dramatically up-regulated in response to peripheral nerve injury. A similar role for apoE in the central nervous system (CNS) has been described whereby apoE distributes cholesterol and phospholipids to neurons after injury. In normal rodent brain apoE is primarily localized to glial cells, whereas in normal human brain apoE has been demonstrated in glia and neurons. After brain injury, intraneuronal apoE is markedly increased in both rodent and human brain. ApoE acts as a ligand for receptors on neurons. The terms "apolipoprotein E" and "apoE" are generically used to refer to either apolipoprotein E protein or gene, and also the terms can refer to any homologs from rat, mouse, rabbit, guinea pig, etc., and their variants.

In humans, three common isoforms of apoE (i.e., apoE2, apoE3, and apoE4) are encoded by the different alleles 2, 3, and 4. The three different apoE isoforms differ only by a single amino acid: apoE2 (cys112, cys158), apoE3 (cys112, arg158) and apoE4 (arg112, arg158). In vitro studies indicate that the three apoE isoforms have differences. Especially, there is a difference in the ability of apoE3 and apoE4 to stimulate neurite outgrowth, bind to amyloid protein, bind to cytoskeletal proteins such as tau and microtubule associated proteins and protect against oxidative stress. In general the apoE4 isoform has a detrimental effect when compared to the apoE3 isoform. For example, in vitro experiments showed that apoE and apoE3 were able to bind to microtubules and form stable complexes with the microtubule associated proteins tau and MAP2c while apoE4 was lacking this ability (Strimmatter et al., *Exp. Neurol.* 125:163–171 (1994)). Current evidence has also identified the apoE4 allele as a major risk factor for sporadic and familial late-onset Alzheimer's disease as well as poor clinical outcome after certain forms of brain injury including that due to head trauma and spontaneous intracerebral hemorrhage. By contrast, possession of an apoE2 has been shown to protect against, or delay the onset of, Alzheimer's disease.

The term "apolipoprotein E4" or "apoE4" refers to apolipoprotein E4 or polymorphic variants, alleles, interspecies homologs, or conservatively modified variants thereof. The terms "apolipoprotein E4" and "apoE4" are generically used to refer to either apolipoprotein E4 protein or gene, as appropriate to the context. Preferably, apoE4 is from a mammal, e.g., rat, mouse, human, rabbit, guinea pig, etc., and their variants. The nucleotide and amino acid sequences of apoE4 are well-known in the art. For example, the human apoE4 gene is known and has the Genbank accession number of M10065.

"Apolipoprotein E4 containing brain cells, or brain tissue containing the same," or "apoE4-containing brain cells, or brain tissue containing the same," refer to brain cells, or brain tissue containing the same, that can express apolipoprotein E4 proteins and/or contain the apoE4 gene, as will be determined from the context. Typically, apoE4-containing brain cells, or brain tissue containing the same, are derived from a transgenic animal that comprises an exogenous apoE gene, e.g., a human apoE4 gene, polymorphic variants, alleles, interspecies homologs, or conservatively modified thereof, which encode an apoE4 protein. The methods for producing these transgenic animals are well-known in the art and described in, e.g., U.S. Pat. No. 6,046,381.

"Brain cells" refers to cells and/or tissue containing the same. Brain cells can be derived from any brain. For example, for use in the methods of the invention, brain cells, or brain tissue containing the same, can be those in or from a normal animal, an apoE-deficient animal, or an apoE4-containing animal. Preferably, brain cells, or brain tissue containing the same, are derived from a mammal, such as a rat, mouse, guinea pig, rabbit, etc. or transgenic animals with modulated levels of neurofibrillary tangles, and/or tau proteins, and/or amyloid, and/or amyloid precursor proteins, and/or cathepsin D levels, and/or cysteine protease levels, and/or mitogen activated kinases, and/or lysosomal enzyme levels, and/or cholesterol levels and/or altered cholesterol metabolism, synthesis, storage, etc. The pathology modeling and drug testing brain cell embodiments of the invention can be carried out in animal models in vivo or in vitro. When provided in an embodiment in which the cells are cultured in vitro, unless otherwise indicated, the brain cells, or brain tissue containing the same, can be provided in any in vitro form capable of culture, for example, brain tissue that contains cells, or brain sections such as slices that contain cells, dissociated cells, cells bound to a solid support or in suspension, etc.

The term "compound that modulates integrins and/or integrin receptors" or "an agent(s) that modulate integrins or integrin receptors" refers to inter alia, a modulator or antagonist that may be selected from the group consisting of neutralizing and/or function blocking agents, such as antibodies to integrin subunits alpha1, alpha2, alpha3, alpha4, alpha5, alpha6, alpha7, alpha8, beta1, beta2, beta3, beta4, beta5, beta6, beta7 and beta8. The compounds of the invention may be further selected from the group of peptides RGD, RGDS (SEQ. ID NO.1), GRGDS (SEQ. ID NO.2), GRGDSP (SEQ. ID NO.3), GRGDTP (SEQ. ID NO.4), mimetics thereof and disintegrins such as echistatin found in snake venom. Preferably the peptides are soluble peptides. Also included are other peptides containing the RGD amino acid motif, and/or other peptides capable of modulating integrin-mediated adhesion, or, alternatively other, non-peptide entities, that are capable of modulating integrins and/or integrin receptors and conservatively modified variants of said peptides. These compounds can be used individually or in a cocktail containing a combination of more than one compound. Sources for the peptides include Calbiochem and Gibco or Life Technologies.

The term a "condition that modulates integrins or integrin receptors" refers to any condition that might accomplish integrin or integrin receptor modulation. In addition to the compounds referred to in the earlier paragraph, additional examples of modulatory compounds include amyloid beta peptide, oxidative free radicals (OH, O2, etc), lysosomal enzyme inhibitors (chioroquine, N-CBZ-L-phenylalanyl-L-alanine-diazomethylketone, NCBZ-L-phenylalanyl-L-phenyl-alanine-diazomethylketon, β-amyloid, and mimetics thereof, etc.), or inflammatory factors (TGFfβ, IL-1β, LPS, etc.). These compounds can be used individually or in a cocktail containing a combination of more than one compound or in combination with the above compounds.

"Conservatively modified variants" applies to both amino acid and nucleic acid sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants and alleles of the invention.

The following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W). (see, e.g., Creighton, Proteins (1984) for a discussion of amino acid properties).

"Antibody" refers to a polypeptide substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes.

Antibodies exist, e.g., as intact immunoglobulins or as a number of well characterized fragments produced by digestion with various peptidases. This includes, e.g., Fab' and F(ab)'2 fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

Antibodies that specifically bind to Aβ can be prepared using any suitable methods known in the art. See, e.g., Coligan, Current Protocols in Immunology (1991); Harlow & Lane, supra; Goding, Monoclonal Antibodies: Principles and Practice (2d ed. 1986); and Kohler & Milstein, Nature 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., Science 246:1275–1281 (1989); Ward et al., Nature 341:544–546 (1989)). Specific polyclonal antisera and monoclonal antibodies will usually bind with a $K_d$ of at least about 0.1 mM, more usually at least about 1 μM, preferably at least about 0.1 IM or better, and most preferably, 0.01 I M or better.

An "Aβ antibody" is an antibody or antibody fragment that specifically binds to one or more epitopes found on Aβ1–42. Preferably, antibody that specifically binds to Aβ1–42 is used in embodiments of the invention, because this antibody recognizes and specifically binds to Aβ.

Examples of antibodies that may be used in the methods of the invention include but are not limited to anti-alpha5, anti-alpha3 and anti-beta1, all of which are available from Chemicon.

"Brain cells" refer to cells and tissues obtained from any brain. For example, brain cells can be obtained from a normal animal, and/or a transgenic animal that comprises an altered endogenous apolipoprotein E gene (one or both alleles) that results in undetectable or significantly less amount of apolipoprotein E proteins. Additionally, brain cells can be obtained from a transgenic animal that comprises, for example, an exogenous apoE gene, e.g., a human apoE4 gene, polymorphic variants, alleles, interspecies homologs, or conservatively modified thereof, which encode an apoE4 protein. Preferably, brain cells are derived from a mammal, such as a rat, mouse, guinea pig, rabbit, etc. Unless otherwise indicated, brain cells can be in the form of brain sections such as slices, dissociated cells, etc. Alternatively, however brain cells can be obtained from primary cell culture prepared from brains of any of the above or established neuronal cell lines.

"Cathepsin D" is a lysosomal protease which typically exists in three forms: the inactive proenzyme having an apparent molecular weight of about 55 kDa; the active single chain having an apparent molecular weight of about 50 kDa; and the active heavy chain having an apparent molecular weight of about 38 kDa. This protease was previously shown to cleave tau protein at neutral (cytoplasmic) pH resulting in tau fragments of approximately 29 kDa. See, e.g., Bednarski & Lynch, J. Neurochem. 67:1846–1855 (1996); Bednarski & Lynch, NeuroReport 9:2089–2094 (1998).

The term "control" refers to the non-treated condition or substance. Control brain cells can be those that are not treated with a compound or agent that can modulate integrins and/or integrin receptors in the brain cells. The term "control" can also refer to brain cells that are not treated with a compound or agent that can interact with glutamate receptors, such as NMDA-type glutamate receptors, in the brain cells. In some embodiments, the term "control" can also refer to brain cells which have been treated with a compound or agent that can modulate integrins and/or integrin receptors in the brain cells, but which have not been treated with a compound or agent that can interact with glutamate receptors, such as NMDA-type glutamate receptors, in the brain cells.

For example, when examining the effect of a compound to determine its ability to have an effect on one or more characteristics of neurodegenerative disease, "control" brain cells could be brain cells that have not been treated with that compound, or brain cells assayed at the beginning of the experiment (time=zero) before any compound-induced changes thereto, as will be clear from the context. In another example, as will be clear from the context, in some embodiments directed to apoE-deficient brain cells or apoE4-containing brain cells, the term "control" brain cells can also refer to normal brain cells (comprising a wild-type or endogenous apolipoprotein E gene) which have been treated with a compound that increases an effective concentration of cathepsin D in the brain cells.

The term "deficient" refers to a decreased or lower amount of the indicated substance. For example, apolipoprotein E "deficient" brain cells, or apoE "deficient" brain cells refer to brain cells that contain less endogenous apolipoprotein E as compared to brain cells having wild-type apolipoprotein E genes (for example, normal brain cells) measured or cultured under similar conditions. The term deficient may also refer to a variant that has an altered function, for example, brain cells that are "deficient" in apoE may contain a variant of apoE that has an altered function, e.g., in lipid transport, as compared to wild-type apoE—such altered function not being able to substitute for the unaltered function.

The term "effective," as in an effective concentration of an "NMDA antagonist" refers to either an amount or an activity of the indicated substance or condition that is sufficient to achieve the indicated purpose. For a first example, an effective concentration a "NMDA antagonist" would be one that produces positive results in terms of alleviating the symptoms of a disease state having at least one of several characteristics as described in this application. Positive results could be determined based on either altering the disease characteristics or could be based on the use of brain imaging techniques, electroencephalographic analysis or cognitive tests.

The terms "identical" or percent "identity," in the context of two or more nucleic acids or polypeptide sequences, refer to two or more sequences or subsequences that are the same or have a specified percentage of amino acid residues or nucleotides that are the same (i.e., 70% identity, preferably 75%, 80%, 85%, 90%, or 95% identity or higher over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "immunoassay" is an assay that uses an antibody to specifically bind an antigen. The immunoassay is characterized by the use of specific binding properties of a particular antibody to isolate, target, and/or quantify the antigen.

"Integrins" are cell surface receptors that mediate the physical and functional interactions between a cell and its surrounding extracellular matrix (ECM). Classically, the role ascribed to integrins has been that of an adhesion molecule, anchoring cells to the ECM. However, the more contemporary spectrum of integrin function greatly exceeds that of mere cell adhesion.

Recent reports have demonstrated that the interaction between the ECM and cell surface integrins leads to intracellular signaling events that affect cell migration, proliferation, and survival, which in the context of neoplastic cells, can translate directly into the malignant phenotype.

By "lysosomal dysfunction" is meant any activity, enzymatic or non-enzymatic, or any property of the lysosomes that is affected in a negative manner relative to a control. This includes vesicle trafficking to or from lysosomes, the endocytic pathway, heterophagy or autophagy, and including the expression and activity of enzymes that are localized in the lysosomes. By "inhibiting or suppressing a lysosomal function" is meant lowering or decreasing one or more such activities from the level or amount of such activity found in the non-inhibited or non-suppressed state, including inhibiting or suppressing vesicle trafficking to or from lysosomes, and including inhibiting or suppressing the expression or activity of a lysosomal enzyme. Such inhibition or suppression can be acute or chronic. Examples of lysosomal enzymes that can be inhibited or suppressed include a lysosomal acid hydrolase, lysosomal protease, lysosomal nuclease, lysosomal lipase, amylase and a cathepsin, cathepsin B, cathepsin H or cathepsin L can be assayed using methods known in the art, for example, as described by Barrett, A. J. et al., *Meth. Enzymol.* 80:535 (1981), Academic Press, New York, incorporated herein by reference.

Lysosomal dysfunction is further described as an abnormal lysosomal morphology, chemistry or activity, which is detrimental to lysosomes or cells. Examples of lysosomal dysfunctions include a detrimental change, either increased or decreased, in the normal activity of the endocytic pathway, a detrimental change in lysosomal morphology, a detrimental change in the intra-lysosomal pH, and/or the activity(ies) of lysosomal enzyme(s).

"Neurodegenerative diseases" include almost all diseases in the central nervous system accompanied by neuronal degeneration and include, e.g., Alzheimer's disease, senile dementia, Parkinson's Disease, Huntingon's Disease, frontotemporal dementias, frontotemporal dementia and Parkinsonism, Pick's disease, Progressive supranuclear palsy pathology, etc. Neurodegenerative diseases also refers to pathologies and/or disorders which are, in part, characterized by features typically associated with human brain aging and related neurodegenerative diseases, such as Alzheimer's disease. Such characteristics include depletion of synaptic proteins, meganeurite formation, induction of neurofibrillary tangles, changes in lysosomal functions and chemistry, e.g., the proliferation of secondary lysosomes filled with lipofuscin, decreases in cathepsin L activities and increases in the levels of cathepsin D, up-regulation and leakage of cathepsin D followed by phosphorylation of variants of tau fragments and accompanying tau proteolysis, activation of microglia, increased levels of sequestration of and/or accumulation of and/or uptake of $A\beta$, etc. Accordingly, "neurodegenerative diseases" can include, e.g., an increased amount of neurofibrillary tangles and/or lysosomes, the appearance of basophilic granules in the mossy fiber terminal zone, the presence of secondary lysosomes with lipofuscin, amyloid deposition, amyloid plaques, neuritic plaques, synaptic loss, neuritic degeneration, neuronal death, increased glial elements and/or increased glial activation (astrocytes, microglia), etc. Brain cells in accordance with embodiments of the invention comprise increased levels of sequestration of and/or accumulation of and/or uptake of $A\beta$, and/or evidence of lysosomal dysfunction, and/or microglia activation, but need not comprise all of these properties to be useful as a model of neurodegenerative diseases.

Embodiments of the present invention are particularly useful as a model of neurodegenerative diseases involving $A\beta$.

"Neurofibrillary tangles" refer to intraneuronal accumulations of filamentous material in the form of loops, coils or tangled masses. Neurofibrillary tangles seen in brain cells in vitro are sometimes referred to herein as "tangle-like structures." While neurofibrillary tangles can also be found during normal aging of the brain, they are found in a significantly higher density in the brain of Alzheimer's disease patients, and other neurodegenerative diseases, such as progressive supranuclear palsy, postencephaltic Parkinson disease, amylotrophic lateral sclerosis, etc. *Robbins Pathologic Basis of Disease,* Cotran et al., 6th ed. (1999), p. 1330. They are commonly found in cortical neurons, especially in the entorhinal cortex, as well as in other locations such as pyramidal cells of the hippocampus, the amygdala, the basal forebrain, and the raphe nuclei. Ultrastructurally, neurofibrillary tangles are composed predominantly of paired helical filaments ("PHF"). A major component of PHF is an abnormally hyperphosphorylated form of the protein tau and tau fragments.

The term "pharmaceutically effective amount" refers to an amount sufficient to alleviate, in any degree or manner, one or more of the manifestations or symptoms recognized or diagnosed as associated with a modifying disorder, modifying manifestations, or a modifying symptom.

The terms "polypeptide,""peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins.

The terms "polypeptide,""peptide" and "protein" include glycoproteins, as well as non-glycoproteins.

The term "reaction" when used to refer to microglial may refer to a transformation of the microglia, for example, from a silent/quiet (slim cell body with ramified thin process) state to an active/macrophage-like (rounded cell body without process) state. Additionally, the term may refer to an enhanced ability to express and secrete cytokines.

The term "sequestration of and/or accumulation of and/or uptake of Aβ" refers to a process, in part, whereby Aβ is physically accreted inside and/or outside of a brain cell. For example, Aβ is added to a medium which comes in contact with brain cells, those contacted brain cells, through biological means, accrete the Aβ within their cell membranes, and/or within their lysosomal bodies, etc. Alternatively, the Aβ containing medium can be contacted with brain tissue and the Aβ in the solution can accrete outside the brain cells, and/or accrete to other elements found outside the brain cells, such as elements of the extracellular matrix, etc.

The phrases "specifically binds to" or "specifically immunoreactive with", when referring to a binding moiety refers to a binding reaction which is determinative of the presence of a target antigen in the presence of a heterogeneous population of proteins and other biologics. Binding moeities include any material capable of resolving the presence of Aβ, such as antibody, dyes, silver, other contrast agents etc. Thus, under designated assay conditions, the specified binding moieties bind preferentially to a particular target antigen and do not bind in a significant amount to other components present in a test sample. Specific binding to a target antigen under such conditions may require a binding moiety that is selected for its specificity for a particular target antigen. A variety of immunoassay formats may be used to select antibodies that are specifically immunoreactive with a particular protein. For example, solid-phase ELISA immunoassays are routinely used to select monoclonal antibodies specifically immunoreactive with an antigen. See Harlow and Lane (1988) *Antibodies, A Laboratory Manual,* Cold Spring Harbor Publications, New York, for a description of immunoassay formats and conditions that can be used to determine specific immunoreactivity. Typically, a specific or selective reaction will be at least twice background signal or noise and more typically more than 10 to 100 times background. Specific binding between an antibody or other binding agent and an antigen preferably has a binding affinity of at least $10^6$ $M^{-1}$. Preferred binding agents bind with affinities of at least about $10^7$ $M^{-1}$, and preferably $10^8$ $M^{-1}$ to $10^9$ $M^{-1}$ or $10^{10}$ $M^{-1}$.

"Transgenic animal" refers to a non-human animal that comprises an exogenous nucleic acid sequence present as an extrachromosomal element or stably integrated in all or a portion of its cells, especially in germ cells.

DETAILED DESCRIPTION OF THE INVENTION

I. Introduction

The present invention provides novel methods for triggering brain cells to induce the conditions of a brain afflicted with a neurodegenerative disease and the brain cells produced by the method. In accordance with embodiments of the invention, brain cells are cultured in a medium which modulates integrins and/or integrin receptors in the brain cells, e.g., by contacting the brain cells with a soluble peptide comprising the amino acid sequence RGD. The modulated integrins and/or integrin receptors in the brain cells then trigger an increased amount of sequestration of and/or accumulation of and/or uptake of Aβ, and/or lysosomal dysfunction, and/or microglia activation.

While some features of neurodegenerative diseases have been reproduced in other in vivo and in vitro models, some key features such as increased sequestration of and/or accumulation of and/or uptake of Aβ, and/or lysosomal dysfunction, and/or microglia activation in the brain cells was often missing in these models. The present invention advantageously provides brain cells wherein the brain cells comprise, among other things, increased amounts of sequestration of and/or accumulation of and/or uptake of Aβ, and/or lysosomal dysfunction, and/or microglia activation.

In the present invention, any suitable brain cells are used. Preferably, brain cells are derived from a mammal, such as rat, mouse, guinea pig, rabbit, etc. Typically, brain cells are derived from normal animals. In certain embodiments transgenic animals can be used, for example, a transgenic animal can be an apoE "knockout" animal, wherein one or both alleles of the endogenous apoE gene is altered or ablated so that the brain cells comprise undetectable or significantly less amount of apoE proteins. Alternatively, brain cells may be derived from transgenic animals that comprise an apoE4 gene (e.g., a human apolipoprotein E4 isoform and its homologs or conservatively modified variants thereof). Preferably, the endogenous apoE genes are completely or partly knocked out in these transgenic animals.

Brain cells, even without the treatment with a compound that modulates integrins and/or integrin receptors, have some residual amount of sequestration of and/or accumulation of and/or uptake of Aβ, and/or lysosomal dysfunction, and/or microglia activation. However, the levels of sequestration of and/or accumulation of and/or uptake of Aβ, and/or lysosomal dysfunction, and/or microglia activation in these untreated brain cells is too low to be regarded as an adequate model for neurodegenerative diseases, such as Alzheimer's disease.

Cathepsin D is a lysosomal protease which is found in the brain, along with other lysosomal proteases, such as cathepsin B and cathepsin L. The activities of these proteases change in the brain with aging. For example, the activity of cathepsin L decreases by up to 90% during brain aging, while the levels and activity of cathepsin D increase. See Nakanishi et al., *Exp. Neurol.* 126:119–128 (1994). Moreover, the activities of these cathepsin proteases are interrelated. For example, it was previously shown that inhibition of cathepsin B and L increases procathepsin D and its maturation into the active two-chain form (composed of heavy and light chain) within lysosomes. See Bednarski & Lynch, *Neuroreport* 9:2089–2094 (1998); Hoffinan et al., *Neurosci. Lett.* 250:75–78 (1998).

Surprisingly, when brain cells are contacted with a compound that modulates integrins and/or integrin receptors, increased sequestration of and/or accumulation of and/or uptake of Aβ were induced in embodiments of the invention. Further, such treatment resulted in evident lysosomal dysfunction including increases in cathepsin D, and such treatments also resulted in the activation of microglia. Typically, the amount of increased sequestration of and/or accumulation of and/or uptake of Aβ, and/or lysosomal dysfunction, and/or microglia activation seen in these treated brain cells is at least twice, sometimes at least ten times greater than the amount of sequestration of and/or accumulation of and/or uptake of Aβ, and/or lysosomal dysfunction, and/or microglia activation seen in normal brain cells not treated with the same compound. The density of sequestration of and/or accumulation of and/or uptake of Aβ, and/or lysosomal dysfunction, and/or microglia activation in these brain cells treated with a compound that modulates integrins and/or integrin receptors is sufficiently high, mimicking the density of sequestration of and/or accumulation of and/or uptake of Aβ, and/or lysosomal dysfunction, and/or microglia activation typically found in the brain of, for example, Alzheimer's disease patients. Since brain cells from transgenic animals contain many aspects and functions when compared to normal brain cells, transgenic brain cells, and brain cells in vivo can also be used in embodiments of the invention.

Brain cells produced in accordance with the present invention have a variety of applications. For example, the brain cells can be used as an assay system to screen agents believed to modulate the amount of sequestration of and/or accumulation of and/or uptake of Aβ, and/or lysosomal dysfunction, and/or microglia activation. These agents can be further tested in other systems and/or in vivo to confirm their efficacy in modulating the sequestration of and/or accumulation of and/or uptake of Aβ, and/or lysosomal dysfunction, and/or microglia activation and possibly other conditions and/or pathologies associated with neurodegenerative diseases, such as the cognitive decline seen in persons afflicted with such disorders. In another example, the brain cells can be used to study the morphological patterns of sequestration of and/or accumulation of and/or uptake of Aβ, and/or lysosomal dysfunction, and/or microglia activation in the brain. In another example, the brain cells can be used to study the effect of sequestration of and/or accumulation of and/or uptake of Aβ, and/or lysosomal dysfunction, and/or microglia activation in normal aging. Such morphological studies would provide additional information regarding the pathological process of aging and neurodegenerative diseases.

II. Production of Characteristics of Neurodegeneration

In one aspect, the invention provides brain cells, or brain tissue containing the same, and methods for producing brain cells, or brain tissue containing the same, to a condition, or contacting brain cells, or brain tissue containing the same, with a compound that modulates integrins and/or integrin receptors to produce and/or increase the sequestration of and/or accumulation of and/or uptake of Aβ, and/or lysosomal dysfunction, and/or microglia activation compared to a control (e.g., brain cells that are untreated with said compound(s)).

Embodiments of the invention include methods comprising:

(a) culturing brain cells; and (b) contacting the brain cells with a compound that modulates integrins and/or integrin receptors, thereby producing properties of an brain afflicted with a neurodegenerative disease, wherein the properties include increased sequestration of and/or accumulation of and/or uptake of Aβ, and/or lysosomal dysfunction, and/or microglia activation, and/or related biochemical changes.

In some embodiments, a method for increasing sequestration of and/or accumulation of and/or uptake of Aβ and/or lysosomal dysfunction, and/or microglia activation in brain cells comprises:

(a) culturing the brain cells in a medium which modulates integrins and/or integrin receptors; and (b) optionally, determining the production of and/or levels of sequestration of and/or accumulation of and/or uptake of Aβ, and/or lysosomal dysfunction, and/or microglia activation.

The brain cells produced in accordance with present methods mimic one or more aspects of brain aging or the brain of patients with Alzheimer's disease or other neurodegenerative diseases, such as the presence of increased levels of sequestration of and/or accumulation of and/or uptake of Aβ, and/or lysosomal dysfunction, and/or microglia activation. However, brain cells produced by the present methods need not mimic all aspects of aged brain or neurodegenerative diseases to be useful as a model of these conditions.

A. Sources of Brain Cells

Any suitable source of brain cells, or brain tissue containing the same can be used in embodiments of the invention. Typically, brain cells, or brain tissue containing the same are derived from a mammal, such as a mouse, rat, guinea pig, rabbit, etc. Brain cells can be derived from a normal animal or other suitable transgenic animals. For example, apoE deficient brain cells or apoE4 containing brain cells can be used in embodiments of the invention. A preferred embodiment includes in vivo brain cells.

Preferably, apoE deficient brain cells or apoE4 containing brain cells are derived from transgenic animals that are genetically modified. For example, the brain cells can be derived from an apoE "knockout" animal, wherein the endogenous apoE gene in the genome has been altered or ablated so that insubstantial or insignificant amount of apoE protein is produced in the brain cells. For example, the function and/or expression of the apoE protein in the apoE "knockout" animal is less than about 30%, preferably less than about 10%, more preferably less than about 5%, still more preferably less than about 1%, compared to a normal animal with the wildtype apoE genes. Most preferably, apoE deficient brain cells are derived from apoE-knockout animals that have no apoE (i.e., null) gene expression.

Typically, apoE4 containing brain cells can be derived from a transgenic animal that comprises an exogenous apoE gene, e.g., a human apoE4 gene, polymorphic variants, interspecies homologs, or other conservatively modified variants thereof. Preferably, in these transgenic animals that comprise an exogenous apoE4 gene, their endogenous apoE gene is completely or partly knocked out.

Transgenic animals comprising apoE deficient brain cells can be produced by recombinant methods known in the art. For example, the endogenous apoE gene function can be altered or ablated by, e.g., the deletion of all or part of the coding sequence, or insertion of a sequence, or substitution of a stop codon. In another example, the non-coding sequence of the apoE gene in the chromosome can be modified by, e.g., deleting the promoter region, the 3' regulatory sequences, enhancers and/or other regulatory sequences of the apoE gene in the chromosome. In yet another example, apoE deficient transgenic animals can be produced by introducing an anti-sense construct that blocks the expression of the endogenous apoE gene products. In some cases, it may be desirable to produce conditional "knock-out" transgenic animals, wherein the alteration in the apoE gene can be induced by, e.g., exposure of the animal to a substance that promotes the apoE gene alteration postnatally. Preferably, both alleles of the apoE gene in the chromosome are altered in these transgenic animals.

The methods for producing transgenic animals are well known and described in, e.g., U.S. Pat. Nos. 5,464,764, and 5,627,059, the disclosures of which are incorporated herein by reference. In particular, the following references describe methods for producing apoE-deficient homozygous rodents: Plump et al., *Cell* 71:343–353 (1992); and Gordon et al., *Neuroscience Letters* 199:1–4 (1995), the disclosures of which are incorporated herein by reference. Moreover, some apoE deficient transgenic animals are commercially available. For example, apoE-deficient homozygous mice, such as C57B1/6J-Apoetm1Unc strain, are available from the Jackson laboratory, Bar Harbor, Me.

Moreover, apoE4 containing brain cells can be derived from a transgenic animal that comprises an exogenous apoE gene. For example, an exogenous apoE gene can be a human apoE4 gene, its interspecies homologs, polymorphic variants, or conservatively modified variants thereof. In human, three isoforms (apoE2, apoE3 and apoE4) express variants of apoE. Among these isoforms, apoE4 is known in the art to encode an apoE protein that is deficient in various functions. For example, compared to apoE3 that stimulates neurite extension, apoE4 was shown to inhibit neurite extension. Nathan et al., *Soc. Neurosci.* 20(Part 2):1033 (1994). It has also been suggested that in vitro tau interacts with apoE3, but not with apoE4. Stritmatter et al., *Exp. Neurol.* 125:163–171 (1994). Moreover, the human apoE4 isoform has been described as a risk factor of Alzheimer's disease (see, e.g., Peterson et al., *JAMA* 273:1274–1278 (1995)). Since brain cells comprising an apoE4 gene appear to lack many normal functions that other apoE isoforms possess, like the apoE deficient brain cells, transgenic animals that comprise an apoE4 gene or its variants may also be used as a source of brain cells in embodiments of the invention.

Such transgenic animals can be produced using various apoE nucleotide sequences known in the art or conservatively modified variants thereof. For example, the human apoE4 gene has the Genbank accession number M10065. The mouse apoE gene has the Genbank accession number D00466. Other homologs or polymorphic variants of apoE genes can also be readily identified. For example, homologs or polymorphic variants of a known apoE gene can be isolated using nucleic acid probes by screening libraries under stringent hybridization conditions. Exemplary stringent hybridization conditions are as follows: a hybridization in a buffer containing 50% formamide, 5×SSC, and 1% SDS, at 42° C., or 5×SSC, 1% SDS, at 65° C., with wash in 0.2×SSC, and 0.1% SDS at 65° C. In some cases, moderately stringent conditions may be used to clone homologs or polymorphic variants of a known apoE gene. An example of a moderately stringent condition includes a hybridization in a buffer of 40% formamide, 1 M NaCl, 1% SDS at 37° C., and a wash in 1×SSC at 45° C. The source of homologs can be any species, e.g., rodents, primates, bovines, canines, human, etc.

In some embodiments, it may be desirable to use modified or mutated versions of apoE genes. For example, a modified version of a human apoE4 gene, when introduced into a transgenic animal, may be capable of producing a higher density of neurofibrillary tangles compared to the unmodified human apoE4 gene. Techniques for in vitro mutagenesis of cloned genes are well-known in the art and can be readily applied for making a modified or mutated apoE gene. See, e.g., Sambrook et al., *Molecular Cloning: A Laboratory Manual,* CSH Press (1989). The functional effect of a modified or mutated apoE gene can be further tested in vivo or in vitro. For example, a transgenic animal comprising a modified or mutated apoE gene can be produced using the methods known in the art. The change in the properties in apoE brain cells (e.g., the neurofibrillary tangle or phosphorylated tau fragment production) can be determined using the methods described below.

Methods for producing a transgenic animal comprising an exogenous apoE gene are known. Generally, an exogenous apoE gene, such as the human apoE4 gene or its variant, is operatively linked to any suitable regulatory element for expressing the apoE4 gene. Preferably, the exogenous apoE gene is operably linked with a mammalian apoE promoter, such as human apoE4 regulatory sequences. This construct can be introduced into an animal using methods known in the art. In these transgenic animals comprising an exogenous apoE gene (e.g., human apoE4 gene), preferably the endogenous apoE gene is partially or completely knocked out so that the endogenous apoE expression or function is insubstantial. Moreover, methods for producing transgenic animals comprising various human apoE isoforms are described in, e.g., U.S. Pat. No.6,046,381 and U.S. Pat. No.5,767,337, the disclosure of which are herein incorporated by reference.

B. Culturing Brain Cells

Brain cells derived from animals described herein can be processed in any suitable manner. For example, the brain can be processed in the form of tissue sections, such as brain slices. Alternatively, the brain tissues can be processed in the form of dissociated cells. Whether in the form of brain slices, dissociated cells, or other forms, they will be generically referred to as "brain cells" herein, unless otherwise indicated.

Additionally, various cell lines may be used in the methods of the invention including integrin knockout cell lines (Matter et al., *J. Cell. Biol.* 141:1019–1030, 1998), human neuroblastoma cell line (IMR-32) (ATCC, Manassas, Va.), CHO and NMDA receptor knockout cells such as NR1-/-and NR2-/-.

In one embodiment, an in vivo model is used. Such in vivo models have an advantage in that they retain the native brain architecture and environment. The effects that are brought about by the methods of the invention are presented against the background of a physiological environment that is more likely to mimic such conditions in humans. In vivo models are also more amenable to long term analysis than are primary cultures, or brain slice cultures. Another advantage is that multiple samples can be taken at the same time from the same animal and from different parts of the brain.

Preferably, the brain is processed in the form of brain slices so that neuronal circuitry or other biological functions are maintained. A suitable thickness of the brain slice is readily determinable by those of skill in the art, and may be varied depending on the culture condition or subsequent analysis methods. For example, the brain can be sliced in the thickness of about 200 μm to about 800 μm, preferably about 350 μm to about 400 μm. The entire brain or portions of the brain can be processed into slices. For example, suitable brain slices may include a hippocampal slice, an entorhinal cortex slice, an entorhinohippocampal slice, a neocortex slice, a hypothalamic slice, or a cortex slice. Since Aβ accumulations tend to develop more prominently in the hippocampal region, a hippocampal slice is preferably used.

Alternatively, the brain can be processed into dissociated brain cells. The entire brain or selected regions of the brain (e.g., the hippocampal region) can be dissociated and maintained in a culture. Generally, the brain tissue is dissected, minced and digested in an enzyme (e.g., trypsin) for a suitable period of time. Then cells are centrifuged and plated at a low density in culture plates. The methods for dissociating cells are well-known in the art. See, e.g., *Freshney, Culture of Animal Cells a Manual of Basic Technique,* 3rd ed., Wiley-Liss, New York (1994), incorporated herein by reference.

Brain cells in the form of slices or dissociated cells can be maintained in culture. Suitable culture conditions for brain cells are well-known in the art. For example, brain cells can be placed onto culture plates, preferably on a support, such as a matrix or membrane, which allows cells to attach. Any suitable medium can be used in maintaining the culture of brain cells. Typically, the culture of brain cells is maintained in a medium that has all the essential nutrients. The culture medium generally has a neutral pH, e.g., between about pH 7.2 to about 7.8, and is maintained at a temperature between about 4° C. to about 40° C., typically at about 37° C. The culture of brain cells is typically maintained in an atmosphere that contains $CO_2$, preferably at 5% $CO_2$. In general, the culture can be maintained for at least about 60 days with a periodic replacement of culture medium.

C. Treatment of Brain Cells with an Agent Capable of Modulating Integrins and/or Integrin Receptors to Trigger the Sequestration of and/or Accumulation of and/or Uptake of Aβ.

To increase the sequestration of and/or accumulation of and/or uptake of Aβ, and/or lysosomal dysfunction, and/or microglia activation, brain cells are contacted with a compound that modulates integrins and/or integrin receptors ("integrin antagonist"). Preferably, a integrin antagonist increases the sequestration of and/or accumulation of and/or uptake of Aβ, and/or lysosomal dysfunction, and/or microglia activation in brain cells by at least about 30%, preferably at least about 50%, more preferably at least about 80%, most preferably at least about 100%, compared to a control (e.g., brain cells untreated with the compound).

Any suitable integrin antagonist compound can be used in embodiments of the invention. The modulator or antagonist may be selected from the group consisting of neutralizing and/or function blocking antibodies for integrin subunits alpha1, alpha2, alpha3, alpha4, alpha5, alpha6, alpha7, alpha8, beta1, beta2, beta3, beta4, beta5, beta6, beta7 and beta8. The methods of the invention are further drawn to a peptide selected from the group of peptides consisting of RGD, RGDS (SEQ. ID NO.1), GRGDS (SEQ. ID NO.2), GRGDSP (SEQ. ID NO.3), GRGDTP (SEQ. ID NO.4), mimetics thereof and disintegrins such as echistatin found in snake venom. Disintegrins block integrin-mediated events in a wide variety of circumstances (Huang, T. F., *Cell Mol Life Sci* 54:527–540 (1998)). Examples of disintegrins include echistatin and triflavin that can be obtained from Sigma.

Other suitable integrin antagonist compounds, and/or agents which modulate integrins and/or integrin receptors are readily determinable by those skilled in the art. For example, a test compound can be contacted with brain cells and/or brain membranes, integrins, integrin receptors, etc. Then the activity or the amount of integrin antagonism can be measured.

The activity or the amount of integrin antagonism is then compared with a control amount (e.g., the amount of integrin-mediated adhesion observed when the assay system is not treated with the test compound). A test compound is referred to as a "integrin antagonist" if it modulates the activity of any one or more of integrins, integrin receptors, etc.) by, e.g., at least about 30%, preferably at least about 50%, more preferably at least about 80%, most preferably at least about 100%, compared to a control.

Brain cells can be contacted with an integrin antagonist compound at any suitable time. For example, brain cells can be contacted with an integrin antagonist compound when the culture is first established, or at a later time after maintaining the culture for a few days. Preferably, brain cells are contacted with an integrin antagonist compound for a period of 1–18 days, preferably for a period of 2–4 days. To induce the sequestration of and/or accumulation of and/or uptake of Aβ and/or lysosomal dysfunction, and/or microglia activation, an integrin antagonist compound is typically added at a concentration of 50 μM to about 5000 μM, more typically at a concentration of about 1 mM to about 3 mM.

Other modulatory compounds, in addition to an integrin antagonist compound(s), can be added in the culture medium to further facilitate the sequestration of and/or accumulation of and/or uptake of Aβ, and/or lysosomal dysfunction, and/or microglia activation or other neurodegenerative features in brain cells. Examples of modulatory compounds include oxidative free radicals ($Fe^{3+}$, $H_2O_2$, etc.), lysosomal enzyme inhibitors (chloroquine, N-CBZ-L-phenylalanyl-L-alanine-diazomethylketone, N-CBZ-L-phenylalanyl-L-phenylalanine-diazomethylketone, and mimetics thereof, etc.), or inflammatory factors (TGFb, IL-1b, LPS, etc.).

Typically, brain cells in a culture are treated with an integrin antagonist under a condition such that the amount of sequestration of and/or accumulation of and/or uptake of Aβ and/or lysosomal dysfunction, and/or microglia activation is increased by at least about 10%, or at least about 20%, or at least about 30%, or at least about 40%, or at least about 50%, or at least about 80%, or at least about 100%, or at least about 150%, or at least about 200%, compared to a control (e.g., brain cells that are cultured in substantially the same condition but without an integrin antagonist compound(s)). Also, brain cells that are treated with an integrin antagonist compound generally produce the sequestration of and/or accumulation of and/or uptake of Aβ, and/or lysosomal dysfunction, and/or microglia activation at a significantly higher level, typically at least two times, sometimes ten times, more than normal brain cells treated with the same compound. Preferably, the treatment conditions (e.g., concentration of integrin antagonist compound(s), the period of incubation, etc.) are selected so that the sequestration of and/or accumulation of and/or uptake of Aβ and/or lysosomal dysfunction, and/or microglia activation produced in treated brain cells is similar to the density of these materials in the brains of patients with Alzheimer's disease, the aging brain, and/or other neurodegenerative diseases.

D. Determining the Sequestration of and/or Accumulation of and/or Uptake of Aβ.

After treating brain cells with an integrin antagonist compound, the levels of sequestration of and/or accumulation of and/or uptake of Aβ, and/or lysosomal dysfunction, and/or microglia activation can be determined if desired. Determination of the sequestration of and/or accumulation of and/or uptake of Aβ, and/or lysosomal dysfunction, and/or microglia activation can be qualitative or quantitative. In some applications, it may be sufficient to visually inspect the sequestration of and/or accumulation of and/or uptake of A-β, and/or lysosomal dysfunction, and/or microglia activation. For example, it may be useful to visually observe the timing and the pattern of sequestration of and/or accumulation of and/or uptake of Aβ, and/or lysosomal dysfunction, and/or microglia activation at different regions of the brain. In other applications, it may be desirable to quantitate the sequestration of and/or accumulation of and/or uptake of Aβ, and/or lysosomal dysfunction, and/or microglia activation. Quantitation would be particularly useful in a screening assay for agents that modulate the sequestration of and/or accumulation of and/or uptake of Aβ, and/or lysosomal dysfunction, and/or microglia activation.

Any suitable methods known in the art can be used to determine the levels of sequestration of and/or accumulation of and/or uptake of Aβ, and/or lysosomal dysfunction, and/or microglia activation. For example, brain cells, in the form of brain slices, dissociated cells, or other suitable forms, can be stained using conventional staining methods. For example, the brain cells can be fixed and stained with a silver stain (Bielschowsky) (Bancroft et al., *Theory and Practice of Histological Techniques*. New York, Churchill Livingstone, Edinburgh, 1996) stain or toluidine blue. Then the stained Aβ, lysosomes, cathepsin D, and/or microglia elements can be visualized by microscopy.

In another example, the brain cells can be stained by immunostaining, and the sequestration of and/or accumulation of and/or uptake of Aβ, and/or lysosomal dysfunction, and/or microglia activation can be visualized. In immunostaining, suitable capture reagents, such as antibodies that specifically bind to Aβ, lysosomes, cathepsin D, and/or microglia elements, can be used. Preferably, antibodies preferentially bind to Aβ, lysosomes, cathepsin D, and/or microglia elements and do not significantly cross-react with other proteins in the brain cells. For example, the antibodies that specifically bind to Aβ, lysosomes, cathepsin D, and/or microglia elements have less than 50%, preferably less than 30%, more preferably less than 10% crossreactivity with other antigens in the brain tissue.

Examples of antibodies that preferentially bind Aβ, lysosomes, cathepsin D, and/or microglia elements include antibodies anti-Aβ1–42, Ab-2 from Calbiochem, ED-1, and other known to those skilled in the art. Preferably, anti-Aβ1–42 is used in embodiments of the invention to bind Aβ, and Ab-2 is used in embodiments of the invention to bind cathepsin D, while ED-1 is used in embodiments of the invention to identify activated microglia.

In immunostaining, an antibody against Aβ, and/or cathepsin D, and/or lysosomes and/or microglia elements is added to brain cells, and the brain cells are incubated for a sufficient time to allow binding between the antibody and Aβ, and/or cathepsin D, and/or microglia elements. The antibody may be labeled with a variety of labels that are detectable. Useful labels include magnetic beads (e.g., DYNABEADS™), fluorescent dyes (e.g., fluorescein isothiocyanate, Texas red, rhodamine, and the like), radio-labels (e.g., $^3$H, $^{125}$I, $^{35}$S, $^{14}$C, or $^{32}$P), enzymes (e.g., horse radish peroxidase, alkaline phosphatase), and calorimetric labels such as colloidal gold or colored glass or plastic beads (e.g., polystyrene, polypropylene, latex, etc.). Alternatively, the antibody may be unlabeled, and a label may be coupled indirectly. For example, an unlabeled primary antibody can be added to the culture to bind Aβ, and/or cathepsin D, and/or lysosomes and/or microglia elements, and then a labeled secondary antibody can be used to amplify the signal for detection.

Means of detecting labels are well known to those of skill in the art. For example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Simple calorimetric labels may be detected simply by observing the color associated with the label.

Alternatively, the levels of Aβ, and/or cathepsin D, and/or lysosomes and/or microglia elements can be determined using cell lysate in an immunoassay. An immunoassay can be performed in any of several formats. These formats include, for example, an enzyme immune assay (EIA) such as enzyme-linked immunosorbent assay (ELISA), a radio-immune assay (RIA), a Western blot assay, or a slot blot assay. For a review of the general immunoassays, see, e.g., *Methods in Cell Biology: Antibodies in Cell Biology*, volume 37 (Asai, ed. 1993); *Basic and Clinical Immunology* (Stites & Terr, eds., 7th ed. 1991). A general overview of applicable technology can also be found in *Harlow & Lane, Antibodies: A Laboratory Manual* (1988). See, also, U.S. Pat. Nos. 4,366,241; 4,376,110; 4,517,288; and 4,837,168.

In one embodiment, an immunoblotting can be used to quantify the amount of Aβ, and/or cathepsin D, and/or lysosomes and/or microglia elements produced in brain cells treated with an integrin antagonist compound. Generally, brain cells are disrupted in an eletrophoresis sample buffer and are treated to obtain a fraction that contains proteins. The proteins are separated by gel electrophoresis and transferred to a membrane that binds the proteins nonspecifically. The location of Aβ, and/or cathepsin D, and/or lysosomes and/or microglia elements on the membrane is determined using, e.g., a labeled primary antibody or an unlabeled primary antibody, followed by a labeled secondary antibody. A detectable label may be, e.g., a radio-label or a fluorescent label or, an enzyme label. Then the membrane comprising a detectable label can be scanned, and digitized images can be quantitatively analyzed by densitometry.

In another embodiment, a sandwich assay can be performed by preparing a brain cell lysate sample, and placing the sample in contact with a solid support on which is immobilized a plurality of antibodies that bind Aβ, and/or cathepsin D, and/or lysosomes, and/or microglia elements. The solid support is then contacted with detection reagents for Aβ, and/or cathepsin D, and/or lysososmes, and/or microglia elements. After incubation of the detection reagents for a sufficient time to bind a substantial portion of the immobilized Aβ, and/or lysososmes, cathepsin D, and/or lysosomes, and/or microglia elements, any unbound labeled reagents are removed. The detectable label associated with the detection reagents is then detected. For example, in the case of an enzyme used as a detectable label, a substrate for the enzyme that turns a visible color upon action of the enzyme is placed in contact with the bound detection reagent. A visible color will then be observed in proportion to the amount of Aβ, and/or cathepsin D, and/or lysosomes and/or microglia elements in the sample.

The above described detection methods are merely exemplary, and other suitable detection methods will be apparent and can be readily substituted by one of skill in the art.

III. Screening Assays

In another aspect, the invention provides methods for screening agents that modulate the sequestration of and/or accumulation of and/or uptake of Aβ, and/or lysosomal dysfunction, and/or microglia activation that are induced by an integrin antagonist compound in brain cells. Particularly useful agents include those that are capable of inhibiting the sequestration of and/or accumulation of and/or uptake of Aβ, and/or lysosomal dysfunction, and/or microglial activation in the brain cells.

Generally, screening methods comprise:

(a) contacting brain cells with an integrin antagonist compound that modulates integrins and/or integrin receptors in the brain cells, wherein the modulated integrins and/or integrin receptors are capable of increasing the amount of sequestration of and/or accumulation of and/or uptake of Aβ, and/or lysosomal dysfunction, and/or microglia activation in the brain cells;

(b) contacting the brain cells with an agent; and (c) determining whether the agent modulates the amount of sequestration of and/or accumulation of and/or uptake of Aβ, and/or lysosomal dysfunction, and/or microglia activation in the brain cells treated with the agent compared to the brain cells that are not treated with the agent.

To produce brain cells comprising increased levels of sequestration of and/or accumulation of and/or uptake of Aβ, and/or lysosomal dysfunction, and/or microglia activation, the methods described in section II above can be used, and these methods will not be repeated in this section. Typically, brain cells in the form of slices are preferably used in the screening assays, since the neuronal circuitry and other biological functions are more intact in brain slices, compared to dissociated brain cells, allowing the brain slices to better mimic the physiological condition of the brain. Preferably, the amounts and/or activities of integrin antagonist compound(s) and other culture conditions are adjusted so that the levels of sequestration of and/or accumulation of and/or uptake of Aβ, and/or lysosomal dysfunction, and/or microglia activation in the brain cells (prior to contacting with an agent) is similar to the density of these materials found in the brains of persons suffering form neurodegenerative diseases, such as Alzheimer's disease.

To screen agents that modulate the sequestration of and/or accumulation of and/or uptake of Aβ, and/or lysosomal dysfunction, and/or microglia activation, brain cells are contacted with a test agent. An "agent" or "substance" refers to any molecule, including, e.g., a chemical compound (organic or inorganic), or a biological entity, such as a protein, sugar, nucleic acid or lipid, that modulates the amount of sequestration of and/or accumulation of and/or uptake of Aβ, and/or lysosomal dysfunction, and/or microglia activation in brain cells. Generally, a test agent or substance is added to the culture medium in the range from 0.1 nM to 10 mM.

Agents can be obtained from a wide variety of sources including libraries of synthetic or natural compounds. For example, libraries of natural compounds in the form of bacterial, fungal, plant and animal extracts can be tested. Known pharmacological agents may be subjected to directed or random chemical modifications, e.g., alkylation, esterification, amidification, etc. to produce a library of structural analogs. Alternatively, a library of randomly or directed synthesized organic compounds or biomolecules (e.g., oligonucleotides and oligopeptides) can be used as a source of agents. Preparation and screening of combinatorial libraries are well known to those of skill in the art. See, e.g., U.S. Pat. No. 5,010,175, PCT Publication No. WO 93/20242, PCT Publication No. WO 92/00091, Chen et al., *J. Amer. Chem. Soc.* 116:2661 (1994), U.S. Pat. No. 5,539,083.

Since the levels of sequestration of and/or accumulation of and/or uptake of Aβ, and/or lysosomal dysfunction, and/or microglia activation is correlated with integrin and/or integrin receptor modulation in brain cells, an integrin antagonist may be effective in increasing the sequestration of and/or accumulation of and/or uptake of Aβ, and/or lysosomal dysfunction, and/or microglia activation or other related neuropathological lesions. Accordingly, a library of putative integrin and/or integrin receptor modulators can be used as a source of agents in a screening assay. Methods for producing a library of potential integrin and/or integrin receptor modulators are known. For example, a combinatorial library of agents against the active site of integrins and/or integrin receptors can be synthesized by one skilled in the art. A library of such agents can be screened by methods in accordance with embodiments of the invention.

An agent can be contacted with brain cells at any suitable time. For example, an agent can be contacted with brain cells prior to contacting the brain cells with an integrin antagonist compound. In another example, the brain cells can be contacted with the agent after the brain cells are contacted with an integrin antagonist compound. Preferably, the brain cells can be contacted simultaneously with the integrin antagonist compound and the agent. Generally, brain cells are contacted with an agent for a period of time sufficient to allow the agent to take an effect. Typically, the brain cells and an agent are contacted for a period of between about 1 minute to about 30 days, preferably between about 30 minutes to about 6 days. Typically, during this time, the culture of brain cells is maintained at a temperature between about 4° C. to about 40° C., preferably at 37° C., at atmosphere containing about 0 to 10% $CO_2$. Other suitable experimental conditions are readily determinable by those skilled in the art.

A number of assays known in the art can be used to determine the effect of candidate agents on the sequestration of and/or accumulation of and/or uptake of Aβ, and/or lysosomal dysfunction, and/or microglia activation in brain cells. For example, various staining or immunoassays described above can be used, and the details of these assay techniques will not be repeated in this section. Other suitable assays will be readily determinable by those of skill in the art, and can be applied in detecting the sequestration of and/or accumulation of and/or uptake of Aβ, and/or lysosomal dysfunction, and/or microglia activation.

In determining whether an agent modulates the integrin antagonist induced sequestration of and/or accumulation of and/or uptake of Aβ, and/or lysosomal dysfunction, and/or microglia activation in brain cells, experiments are typically carried out with a control. A control can be, e.g., adding no agent or adding a different amount or type of agent is added and extrapolating and determining the zero amount. A statistically significant difference in a test amount (e.g., brain cells treated with a test agent) and a control amount (e.g., brain cells untreated with a test agent) of sequestration of and/or accumulation of and/or uptake of Aβ, and/or lysosomal dysfunction, and/or microglia activation indicates that the test agent modulates the sequestration of and/or accumulation of and/or uptake of Aβ, and/or lysosomal dysfunction, and/or microglia activation. For example, inhibition of sequestration of and/or accumulation of and/or uptake of Aβ, and/or lysosomal dysfunction, and/or microglia activation is achieved when the test amount of sequestration of and/or accumulation of and/or uptake of Aβ, and/or lysosomal dysfunction, and/or microglia activation relative to the control amount is about 90% (e.g., 10% less than the control), optionally 80% or less, 70% or less, 60% or less, 50% or less, 40% or less, or 25–0%.

Brain cells in accordance with embodiments of the invention provide an in vitro model for neurodegenerative diseases, such as Alzheimer's disease, and brain aging. As such, brain cells contacted with integrin antagonists provide a cost and time efficient in vitro model to study such diseases. For example, brain cells produced in accordance with embodiments of the invention can be advantageously used to screen agents that may modulate the sequestration of and/or accumulation of and/or uptake of Aβ, and/or lysosomal dysfunction, and/or microglia activation in the brain cells. Efficacious agents that are identified by in vitro screening methods described herein can be further tested to determine their efficacy in vivo. Some of these agents can potentially be useful as therapeutic compounds for neurodegenerative diseases, including Alzheimer's disease.

The following examples are offered by way of illustration, not by way of limitation.

EXAMPLE 1

I. Materials and Methods

A. Preparation and Maintenance of Hippocampal Slice Cultures

Organotypic hippocampal cultures were prepared using the technique of Stoppini et al. (1991). Briefly, hippocampi were harvested from brains of 9–12 days old Sprague-Dawley rat pups under sterile conditions. Sections were cut (400 μm thick) perpendicular to the long axis of hippocampus using a McIllwain tissue chopper and were collected into a cutting medium consisting of MEM with Earle's salts (Gibco, Rockville Md.), 25 mM HEPES, 10 mM Tris base, 10 mM glucose, and 3 mM MgCl2 (pH 7.2). Slices were positioned onto 30 mm cell culture inserts (Millicell-CM, Millipore, Bedford, Me.) that were placed in 6 well culture trays with 1 ml of growth medium per well [growth medium: MEM with Hank's salts (Gibco), 20% horse serum, 3 mM glutamine, 25 mM HEPES, 5 mM NaHCO3, 25 mM glucose, 0.5 mM ascorbate, 2 mM CaCl2, 2.5 mM MgCl2, 0.5 mg/l insulin, and penicillin, pH 7.2]. The cultures were incubated at 35° C. with a 5% CO2-enriched atmosphere and the media was changed every other day until use 10–12 days later.

B. Treatment with Aβ and Integrin Antagonist

Cultured hippocampal slices were exposed to media containing the human Aβ1–42 sequence in the presence or absence of the integrin antagonist peptide, Gly-Arg-Gly-Asp-Ser-Pro, or GRGDSP (SEQ. ID. No.3) (2 mM dissolved in media) (Ruoslahti, E., *Ann Rev Cell Dev Biol* 12:697–715 (1996)). In some cases, slices were co-treated with the specific NMDA receptor antagonist 2-amino-5-phosphonovalerate (AP5) (Sigma) at 50 μM. Control slices in neighboring wells received media-vehicle only. Aβ1–42 peptide solution was freshly prepared before the start of the experiment using 0.1N NaOH, pH adjusted with 0.1N HCl to 7.4, and then diluted with serum-free culture medium. Aβ was applied at 30 μM for 8–10 hr after which it was diluted to 15 μM by the addition of fresh culture media containing heated treated horse serum. Treatment was repeated every other day for a total 6 days. Disintegrins are small (4–10 kDa) RGD-containing, cysteine-rich peptides from snake venom that bind integrins with high affinity (Kd~1 nM–0.1 μM) and are potent antagonists of integrin functions (Huang, T. F., *Cell Mol Life Sci* 54:527–540 (1998)for review). In some experiments the disintegrin echistatin (2 μM dissolved in media) was applied instead of GRGDSP (SEQ. ID. No.3). To further test the specificity of the integrin antagonists, the inactive control peptide Gly-Arg-Ala-Asp-Ser-Pro (GRADSP) (Torimoto, Y., et al., *J Exp Med* 172:1315–1323 (1990)) was used at 2 mM.

C. Immunocytochemistry

The following treatment, slices were thoroughly washed with 0.1M sodium phosphate buffered saline (PBS), fixed for 12–16 hr in cold 0.1M phosphate buffer (PB; pH 7.2) containing 4% paraformaldehyde, cryoprotected in 20% sucrose/PB for 1–2 hr and then carefully removed from the insert membranes. Serial sections were cut at 25 μm thick, parallel to the broad face of the explant, using a freezing microtome. Immunocytochemistry was performed using the standard avidin biotin horseradish peroxidase complex (ABC) method using reagents and instructions of the VECTASTAIN® Elite ABC kit from Vector Laboratories (Burlingame, Calif.) with diaminobenzidine tetrahydrochloride (0.05% in 50 mM Tris-HCl buffer, pH 7.4) as chromagen and PBS for rinses and as diluent for antibody incubations. Briefly, free-floating sections were preincubated with 3% normal goat serum (for anti-Aβ1–42 and anti-cathepsin D antibodies) or 10% normal horse serum (for ED-1) in PBS for 1 hr at room temperature. Sections were then incubated with anti-human Aβ1–42 (1:5000, gift from Dr. C. Glabe, UCI; specific for the human Aβ1–42 sequence; does not recognize rat amyloid peptides), anti-cathepsin D (1:100, Calbiochem, San Diego) antisera in 1.5% normal goat serum or monoclonal antibody ED-1 (1:1000; Serotec, Oxford) in 5% normal horse serum overnight at 4° C. Sections were washed in PBS, incubated in biotinylated anti-rabbit or anti-mouse IgG (both at 1:200) for 2–3 hr, washed in PBS, incubated in the avidin-biotin complex solution for 45 min and then processed through the diaminobenzidine reaction. After final rinses in PBS, sections were mounted on Super-Frost Plus slides (Fisher Scientific, Pittsburgh), air-dried, dehydrated in a series of graded ethanols, and coverslipped from Clearing Solvent (Stephens Scientific, Kalamazoo, Mich.) with Permount (Fisher).

In some cases a dual-chromogen procedure was used for simultaneous immunolabeling of Aβ1–42 and the microglial antigen ED-1. Briefly, sections were first immuno stained with anti-As 1–42 using diaminobenzidine tetrahydrochioride as the chromagen (as above) to yield a dark grey reaction product within the labeled neurons. The sections were then washed with PBS, and immunostained for ED-1 following the same steps up to the chromogen reaction. At this point, the sections were processed through several changes of 0.02 M PB, pH 6.5, to lower the pH and ionic strength, and were then incubated with 0.005% benzidine dihydrochioride and 0.001% hydrogen peroxide to yield granular blue-black deposits.

To control for potential non-specific labeling in immunostaining procedures, tissue was processed through all steps but with the primary antisera replaced by PBS or normal sera in the first incubation. No cellular or regional labeling was observed under these conditions.

Photomicrographs were obtained using an Olympus AX70 microscope and Kodak PlusX film (Kodak, Rochester, N.Y.). Film images were then digitized using a Portland scanner and figures were prepared by using Adobe Photoshop (version 5.5): only brightness and contrast were modified to create panels of comparable density in the final illustrations.

D. Quantification and Statistical Analyses

To compare the effects of integrin antagonists on Aβ1–42 internalization, quantification of Aβ1–42-ir elements was conducted for stained explants from four separate experiments that each included the following treatments: Aβ1–42 only (n=8 explants), Aβ1–42 plus the inactive peptide GRADSP (n=9), Aβ1–42 plus the integrin antagonist peptide GRGDSP (SEQ. ID. No.3) (n=19), or Aβ1–42 plus echistatin (n=12). Images centered on CA1b stratum pyramidale were obtained at 40× objective magnification using a Sony DKC-5000 digital camera attached to a Zeiss Universal microscope. The full digital images were then analyzed using the densitometric capabilities of the National Institutes of Health Image 1.60 software on a G4 Macintosh computer. The "density slice" t option was used to threshold CA1 areas so that only immunolabeled "objects" were selected. The areas and mean density of selected particles for each image were then quantified using the "analyze particles" option. All images from the different treatment groups to be compared were digitized using the same acquisition parameters and the same threshold density setting. Group mean values were obtained and statistical significance was evaluated using the 2-tail Student's paired t test. Significance was set at $p<0.05$.

II. Results

1. Uptake of Aβ1–42 is Enhanced by Integrin Antagonists

Figure 1:
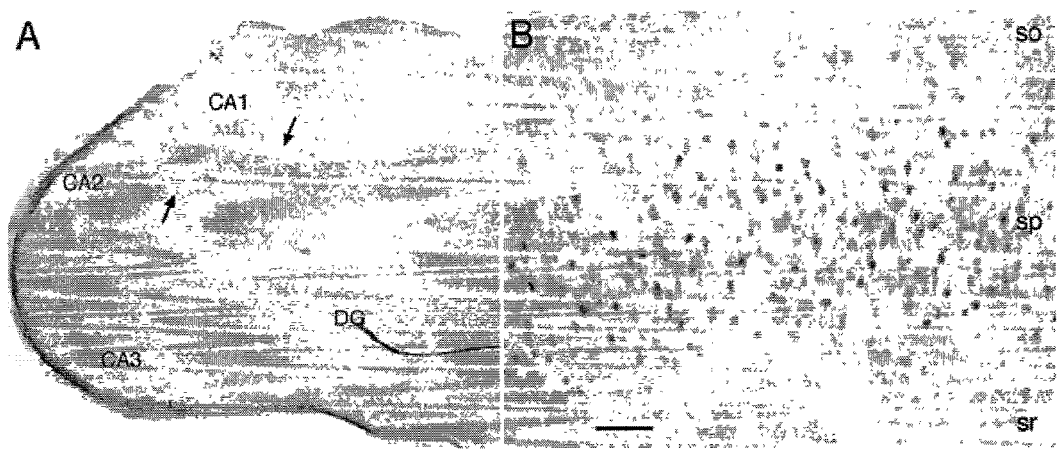
FIG. 1A–B. Modest internalization of Aβ in hippocampal slices treated with Aβ1–42 only.

Cultured hippocampal slices were incubated in parallel for six days under one of the following treatment conditions: (1) vehicle (control); (2) Aβ1–42; (3) GRGDSP (SEQ. ID. No.3); and (4) Aβ1–42 plus GRGDSP (SEQ. ID. No.3), as described in Methods, and were then processed for the immunohistochemical localization of incorporated human Aβ1–42. No Aβ immunostaining was detected in vehicle-treated control slices. Intraneuronal Aβ1–42 immunoreactivity (Aβ-ir) was detected in 42% [19/45] of the slices incubated with Aβ1–42 alone (Table 1). Staining was restricted almost exclusively to field CA1, where it was located in neuronal perikarya and proximal dendrites. As shown in FIG. 1, labeling was found in discrete 'mediolateral' segments of stratum pyramidale (see field bracketed by arrows in FIG. 1A). The restricted distribution of uptake is in agreement with previous reports (Bahr, B., et al., *J Comp Neurol* 397:139–147 (1998)). Serial sections established the further point that labeling was densest in the superficial third of the Aβ-treated slices (not shown). Examination at higher magnification showed that the antisera densely labeled a relatively homogenous population of punctate bodies that were smaller than normal pyramidal cell somata (see FIG. 1B) and more lightly labeled a few processes in CA1 stratum radiatum. Based on the size and somatic location of the Aβ-ir puncta, it appeared that immunostaining was concentrated in lysosomes.

TABLE 1

Antagonist Effects on Internalization of Aβ$_{1-42}$

|  | Control | Aβ | RGD | Aβ + RGD | Aβ + RAD | Aβ + Ech | Aβ + RGD |
|---|---|---|---|---|---|---|---|
| number of slices tested | 31 | 45 | 14 | 61 | 16 | 21 | 16 |
| Aβ positive cases | 0 | 19 | 0 | 54 | 9 | 18 | 0 |

Figure 2:
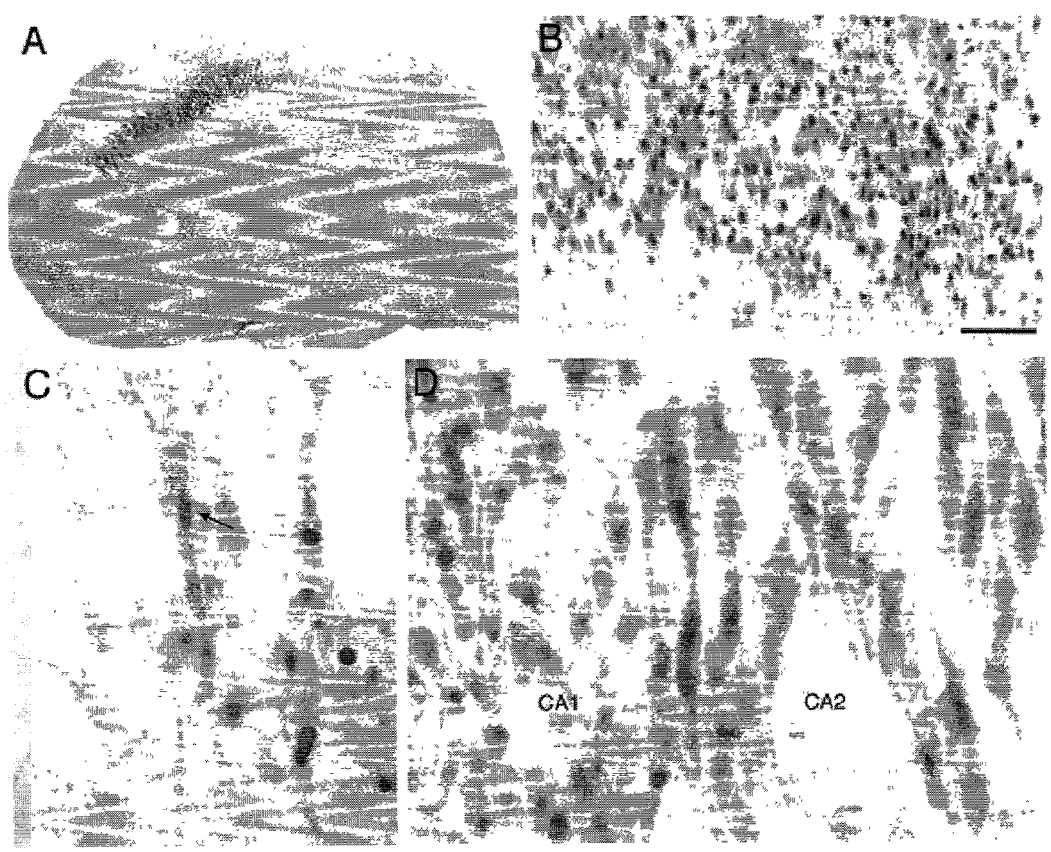
FIG. 2A–2D. Exogenous Aβ incorporation is enhanced by the integrin antagonist GRGDSP (SEQ. ID. No.3). Photomicrographs of sections from an explant treated with Aβ1–42 plus 2 mM GRGDSP (SEQ. ID. No.3) for 6 days and processed for the localization of Aβ-ir.
Figure 3:
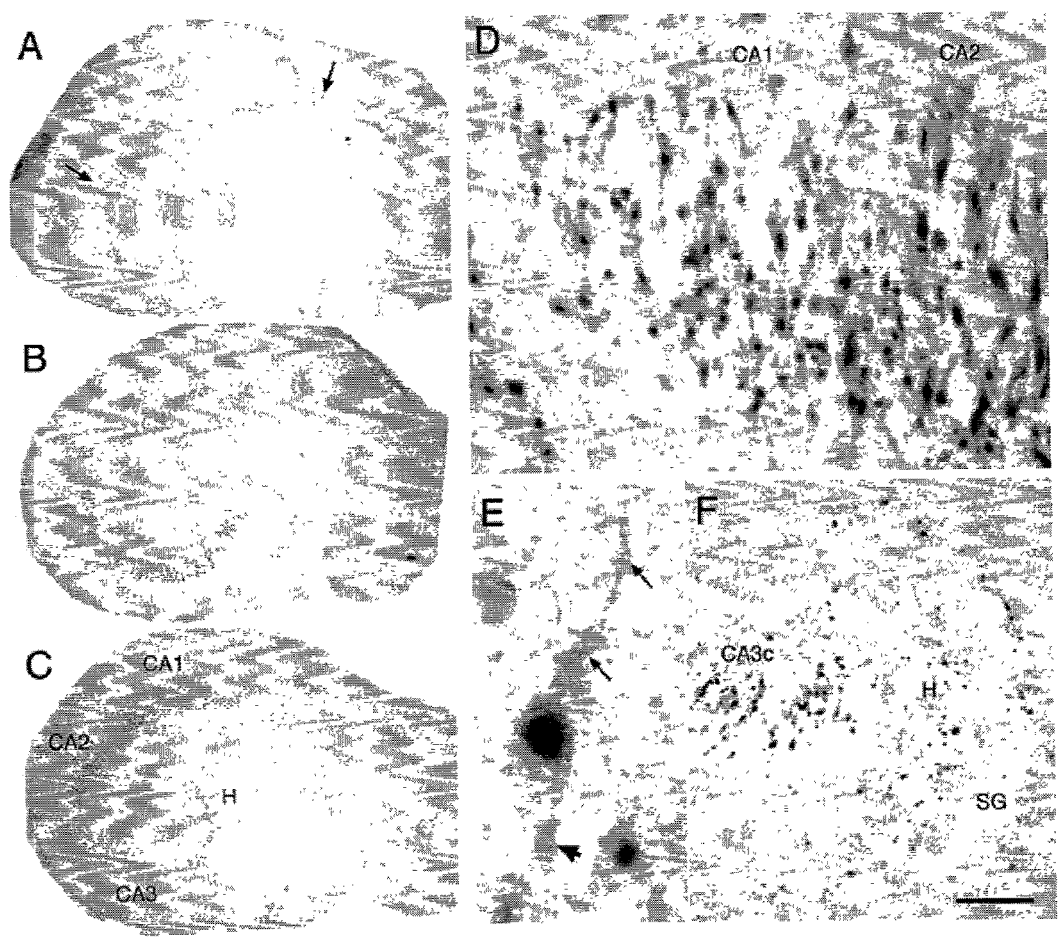
FIG. 3A–3F. Facilitation of Aβ internalization is specific to integrin antagonists. Photomicrographs of Aβ-ir in cultured hippocampal slices incubated with Aβ1–42 in the presence of the inactive control peptide GRADSP (SEQ. ID. No.5), (FIG. 3A), the disintegrin echistatin or (FIG. 3B) or the peptide integrin antagonist GRGDSP (SEQ. ID. No.3) (H, dentate gyrus hilus). Note that both antagonists of the RGD-binding integrins, GRGDSP (SEQ. ID. No. 3) (FIG. 3C) and echistatin (FIG. 3B), increased the uptake of Aβ1–42 peptide and led to incorporation within both fields CA3 and CA1, whereas incorporation in the presence of GRADSP (SEQ. ID. No. 5) (FIG. 3A) was modest and limited to the CA2 and subicular boundaries of CA1 stratum pyramidale (FIG. 3A, arrows). Panel D shows Aβ1–42-ir at the border between fields CA1 and CA2 from a slice treated with echistatin illustrating the clustering of Aβ-ir around nuclei in field CA1 and the more diffuse appearance of cytoplasmic staining in pyramidal cells of field CA2: Similar regional differences are seen in slices treated with GRGDSP (SEQ. ID. No.3). (E) Subicular neuron from an explant incubated with GRGDSP (SEQ. ID. No.3) and Aβ1–42 showing the dense accumulation of Aβ-ir in granules around the nucleus and lighter labeling in swellings along the apical dendrite (small thin arrows) and axon (short arrow). (F) Aβ immunostaining of neurons in the dentate gyrus from a slice treated with GRGDSP (SEQ. ID. No.3) and Aβ1–42 showing scattered labeled cells in CA3C stratum pyramidale, the central hilus (H) and the surrounding stratum granulosum (SG). The scale bar used in FIG. 3F=0.5 mm in FIG. 3A–3C; 50 μm in FIG. 3D; 18 μm in FIG. 3E and 80 μm in FIG. 3F.

The GRGDSP (SEQ. ID. No.3) peptide by itself did not induce Aβ-ir but did markedly increase sequestration of the exogenous peptide. More than 88% of the slices treated with Aβ1–42 plus 2 mM GRGDSP (SEQ. ID. No.3) [i.e., 54/61] had significant intraneuronal immunostaining (Table 1), a percentage that was significantly greater ($p<0.0001$, Fisher's test) than that found in explants treated with the Aβ peptide only. In further contrast to slices treated with Aβ-alone, labeling was detectable throughout the depth of the slice and was both more dense and more broadly distributed (FIG. 2A), in some instances extending into fields CA2 and CA3 (FIG. 3C). FIG. 2 further illustrates Aβ sequestration patterns in slices treated with Aβ1–42 plus GRGDSP (SEQ. ID. No.3). Labeling was uniformly dense throughout the pyramidal cell layer of CA1 (FIG. 2A) but was not found in interneurons scattered throughout the apical and basal dendritic fields. Internalized Aβ-ir in CA1 pyramidal neurons formed discrete packets in the perinuclear cytoplasm (FIG. 2B–D); these elements were noticeably larger than the punctate structures stained in slices treated with Aβ alone. FIG. 2C illustrates this point. The arrow points to a dense accumulation of Aβ1-ir that stretches across the shaft of an apical dendrite; similar sized deposits can be seen in neighboring neurons. Immunopositive structures of this magnitude were never found in the slices treated with Aβ alone.

FIG. 2C also illustrates the point that in slices treated with Aβ1–42 plus GRGDSP (SEQ. ID. No.3), punctate Aβ-ir was accompanied by lighter, diffuse cytoplasmic immunostaining. As shown, Aβ-ir extended throughout the cell body and well into both apical and basal dendritic trees. The balance of punctate vs diffuse staining varied between hippocampal subfields. FIG. 2D shows the border between fields CA1 and CA2 and, as can be seen, discrete immunopositive structures were more prevalent in the former region. In some cases, incorporated Aβ1–42 was found within neurons that exhibited dendritic and axonal swellings (arrows in FIG. 3E). FIG. 3F shows the dentate gyrus from a GRGDSP (SEQ. ID. No.3) plus Aβ1–42-treated slice; Aβ1-ir was observed mainly in neurons scattered throughout the central and subgranular hilus although a few labeled cells were observed in stratum granulosum as well.

To further test the conclusion that GRGDSP (SEQ. ID. No.3) effects are due to integrin antagonism, the effects of another small peptide, GRADSP, and of the disintegrin echistatin were examined. The GRADSP peptide, which is a very weak antagonist of integrin binding to fibronectin and vitronectin and is typically used as an inactive control peptide (Pierschbacher, M., and Ruoslahti, E., *Nature* 304: 30–33 (1984); Ruoslahti, E., *Ann Rev Cell Dev Biol* 12:697–715 (1996); Bahr, B. A., et al., *J Neurosci* 17:1320–1329 (1997)), did not measurably affect sequestration of Aβ1–42 (FIG. 3A; Table 1). Disintegrins are small (4–10 kDa) RGD-containing, cysteine-rich peptides from snake venom that bind integrins with high affinity (Kd~1 nM-0.1 μM). They block integrin-mediated events in a wide variety of circumstances and are much more potent in this regard than GRGDSP (SEQ. ID. No.3) peptide (Huang, T. F., *Cell Mol Life Sci* 54:527–540 (1998) for a review). Previous work has shown that injection of 5 μM echistatin with a microsplitzer selectively disrupts LTP stabilization in field CA1 of hippocanipus (Chun et al., 2001). As shown in FIG. 3B, incubation with echistatin at 2 μM significantly enhanced Aβ internalization and, like GRGDSP (SEQ. ID. No.3) (FIG. 3C), expanded the zone of incorporation to include field CA3; Aβ1–42-ir was observed in 86% of echistatin plus Aβ1–42 treated slices (18/21) (Table 1). At higher magnification one can see the distribution of intraneuronal Aβ1–42-ir in echistatin treated slices (FIG. 3D) is similar to that induced by GRGDSP (SEQ. ID. No.3) (FIG. 2D).

Figure 4:
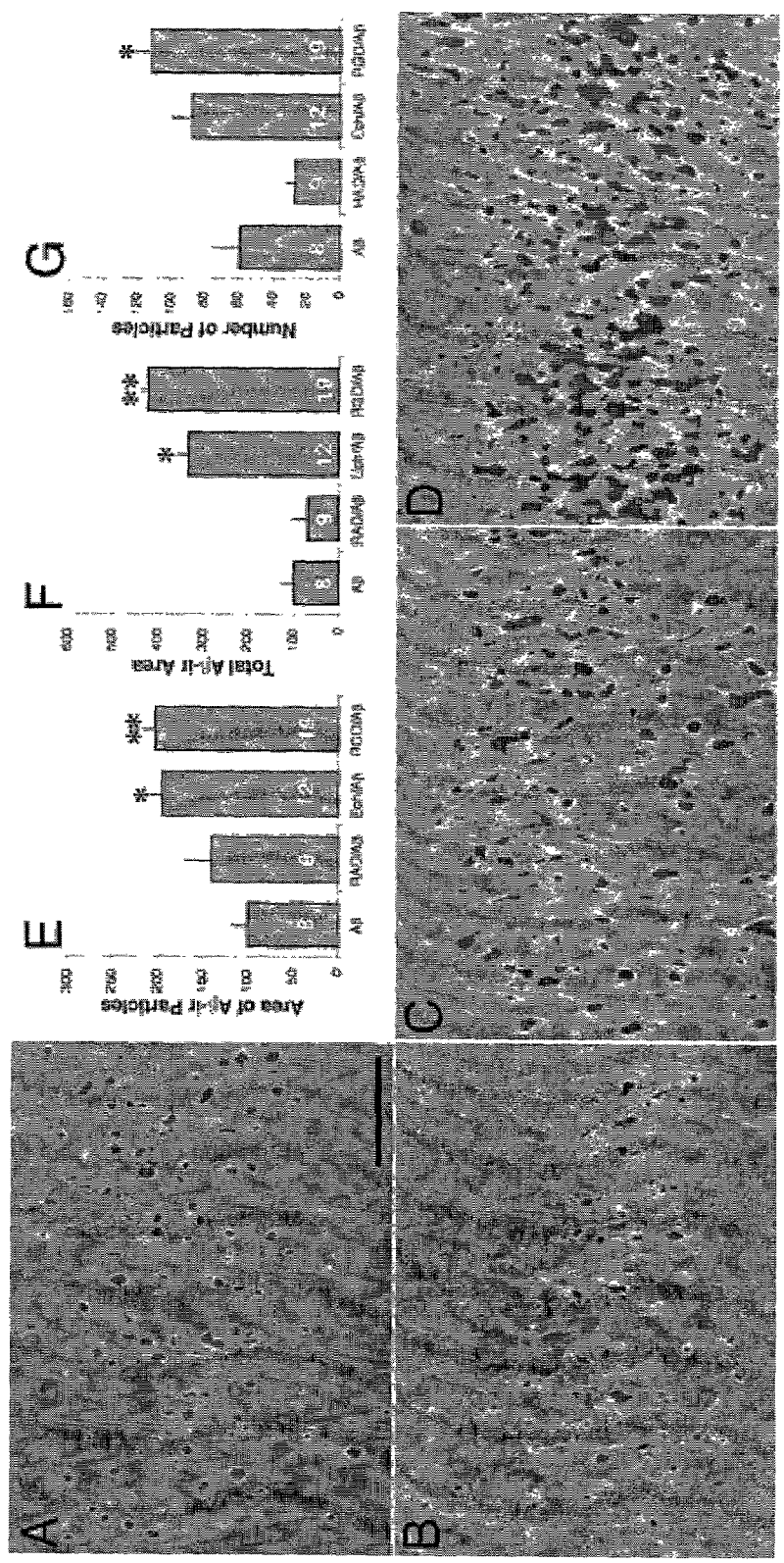
FIG. 4A–4G. A survey and quantification of Aβ-1–42 uptake in four treatment groups; Aβ1–42 alone (FIG. 4A) or in the presence of GRADSP (SEQ. ID. No.5) (FIG. 4B), echistatin (FIG. 4C), or GRGDSP (SEQ. ID. No.3) (FIG. 4D).

Quantitative analyses of levels of Aβ-ir in cultured slices verified the above impressions of drug effects. As described in the Methods section, the "density slice" function of the NIH Image program was used to calculate the numbers and overall area of Aβ-ir elements, at or above a specific staining density, within a fixed-sized field of CA1 stratum pyramidale. The same density threshold was used for all slices from the different treatment groups. FIGS. 4A–D show representative images from slices treated with Aβ alone, Aβ plus GRADSP, Aβ plus echistatin, and Aβ plus GRGDSP (SEQ. ID. No.3), respectively; in each case elements counted as being immunolabeled at or above the threshold density are highlighted in black. Results of quantitative analyses are shown in FIG. 4, graphs E through G, which show the average area of individual Aβ1-ir particles (E), the total area encompassed by Aβ-ir elements (F) and the number of Aβ-ir elements within the sample field (G), respectively. Incubation of hippocampal cultures with the integrin antagonists echistatin and GRGDSP (SEQ. ID. No.3) significantly enlarged the size of Aβ1-ir elements [+95±13% and +101±13% (mean±sem); $p<0.05$ and $p<0.01$, respectively; 2-tail t-test] (FIG. 4E) and increased the total area encompassed by immunoreactive elements [233±24%, $p<0.05$ and 324±16%, $p<0.01$; 2-tail t-test, respectively] (FIG. 4F). Moreover, as shown in FIG. 4G, both antagonists increased the numbers of Aβ-ir particles although this effect was statistically significant for GRGDSP (SEQ. ID. No.3) only. These results indicate that disruption of integrin mediated cell adhesion not only increases intraneuronal levels of Aβ but also recruits more neurons into Aβ uptake processes. Incubation with the control peptide GRADSP did not cause significant changes in either the areas or numbers of Aβ-ir elements (FIG. 4).

2. Enhanced Uptake of Aβ Increases Cathepsin D and Activates Microglia

Increases in cathepsin D are reported for AD brains (Cataldo, A. M., et al., *Neuron* 14:671–680 (1995); Callahan, L. M., et al., *J Neuropathol Exp Neurol* 58:275–87 (1999); Ginsberg, S. D., et al., *Ann Neurol* 48:77–87 (2000)) and were used to assess whether enhanced Aβ1–42 sequestration produced by integrin antagonists generates age-related pathology. Six day treatments with Aβ1–42 by itself did not cause substantial increases in cathepsin D-ir in any segment or collection of cells within cultured slices (n=5; FIG. 5A). However, in the presence of 2 mM GRGDSP (SEQ. ID. No.3), Aβ1–42 generated intense intraneuronal cathepsin D-ir (arrows in FIG. 5B). Elevated immunostaining was localized to puncta that had the distribution and approximate size expected for lysosomes (FIG. 5C, inset). Labeling was more prominent in, but not restricted to, field CA1. Treatment with 2 mM GRGDSP (SEQ. ID. No.3) alone did not increase cathepsin D-ir.

In addition to the dense neuronal immunostaining, elevated cathepsin D-ir was also localized in patches within small irregularly distributed cells that had short processes and small cell bodies (arrowheads in FIG. 5C). Based on their size, distribution and morphology, these cathepsin D-ir cells appeared to be microglia. Immunopositive elements of this type were not observed in slices treated with Aβ1–42 or GRGDSP (SEQ. ID. No.3) alone.

Figure 6:
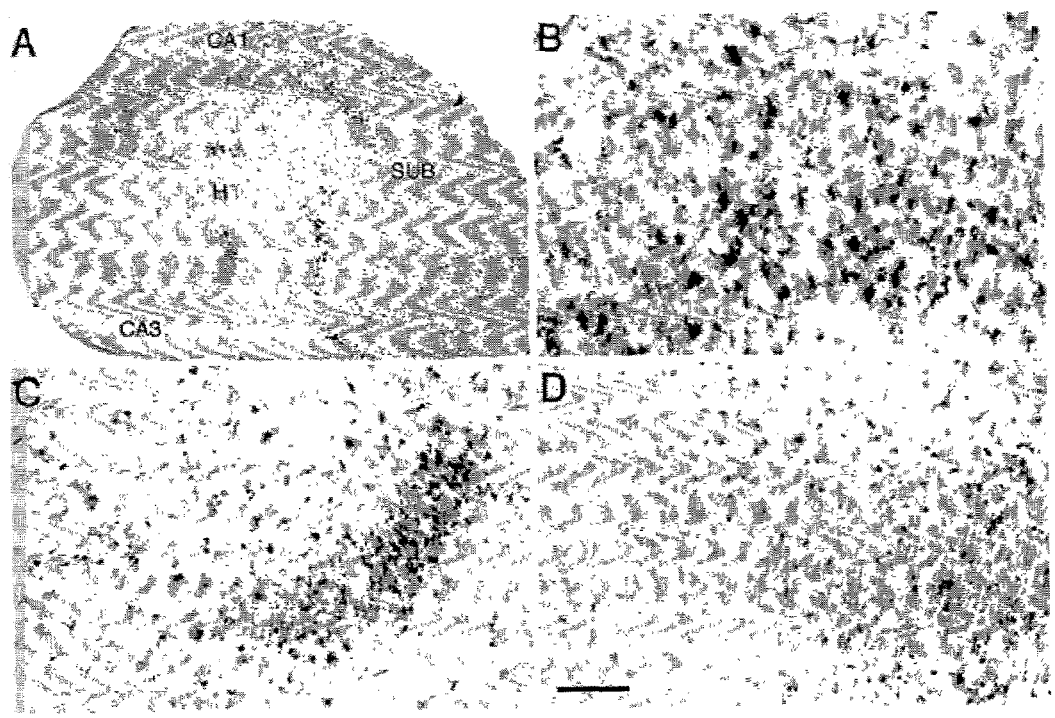

Alzheimer disease is also associated with a brain inflammatory response [see (Akiyama, H., et al., *Neurobiol Aging* 21:383–421 (2000)) for a recent review], one component of which involves microglia (Cras, P., et al., *Brain Res* 558: 312–314 (1991)). To test if uptake of Aβ induces inflammatory activity, and specifically activates microglial cells, double staining was carried out using anti-Aβ1–42 sera and monoclonal antibody ED-1, a marker for lysosomal membranes within reactive microglia (Kato, H., et al., *Brain Res* 694:85–93 (1995); Woods, A. G., et al., *Neurosci* 91:1277–1289 (1999)); this yielded dark grey and black reaction products for Aβ-ir and ED-1ir, respectively (FIG. 6). Aβ1–42 and GRGDSP (SEQ. ID. No.3) by themselves did not cause a noticeable increase in the number of ED-1 positive cells but applied together produced a pronounced microglial response (FIG. 6A). ED-1-ir microglia were observed mainly in fields CA1 (FIG. 6B) and CA3c (FIG. 6C); these cells had "reactive" features including a rounded and enlarged cell body and shortened processes. The Aβ1–42- and ED-1-immunoreactivities were not colocalized within individual cells indicating that the microglia did no internalize Aβ at detectable levels, importantly, however, ED-1 positive microglia were co-distributed with Aβ-ir neurons. That is, large numbers of labeled microglia were found intermingled with populations of Aβ immunostained neurons. These co-distributed cells were most frequently found in subregions of field CA1 but fields of overlapping labeled cells were occasionally distributed within in CA2, CA3 and subiculum as well. Areas lacking Aβ-ir neurons were nearly devoid of ED-1 positive microglia, as shown on the left side of FIG. 6D.

3. Uptake and Effects of Aβ1–42 are Blocked by an NMDA Receptor Antagonist

Activation of the NMDA-class glutamate receptors allows calcium influx and facilitates internalization of membrane protein (Carroll, R. C., *Proc Natl Acad Sci USA* 96:14112–14117 (1999); Beattie, E. C., et al., *Nat Neurosci* 3:1291–300 (2000); Ehlers, M. D., *Neuron* 28:511–25 (2000)). A selective antagonist of NMDA receptors, AP5, was used to test if NMDA receptors are involved in GRGDSP-enhanced (SEQ. ID. No.3) Aβ1–42 uptake. FIG. 7 shows Aβ1–42 immunostaining in sections from slices that had been incubated in parallel with Aβ1–42 plus GRGDSP (SEQ. ID. No.3) with (FIG. 7A') or without (FIG. 7A) AP5. As shown, the NMDA receptor antagonist completely blocked Aβ1–42 uptake. Comparable results were obtained in 16 experiments, the total of this type conducted.

FIGS. 7B' and 7B compare immunostaining for cathepsin D in slices incubated with Aβ1–42 and GRGDSP (SEQ. ID. No.3) in the presence or absence of AP5, respectively. As shown, intraneuronal cathepsin D-ir was almost totally suppressed in the slice exposed to AP5 (FIG. 7B'). Note also that cathepsin D immunostaining of presumed microglia is also absent from the experimental slice, as expected if this effect was secondary to neuronal uptake and consequent neuronal pathology. Similarly, ED-1-ir microglia were also greatly reduced in AP-5 co-treated slices (FIG. 7C'). Thus, each of the AD-like changes that otherwise accompany GRGDSP-enhancement (SEQ. ID. No.3) of Aβ1–42 uptake were blocked by the NMDA receptor antagonist AP5.

III. Discussion

Uptake of Aβ is Enhanced by RGD-binging Integrin Antagonists

The principal integrin antagonist used herein (i.e., GRGDSP (SEQ. ID. No.3)) was reported to block the binding and uptake of Aβ in CHO cells in culture (Matter, M. L., et al., *J Cell Biol* 141:1019–1030 (1998)) but, as described here, markedly enhances uptake in cultured hippocampal slices. The majority of slices under control conditions did not accumulate appreciable concentrations of Aβ1–42 during six-day incubations. Moreover, when substantial uptake did occur, it was restricted both with regard to depth in the slice and to hippocampal subdivision (i.e., CA1 stratum pyramidale), which is in agreement with the previous studies (Bahr, B., et al., *J Comp Neurol* 397: 139–147 (1998); Harris-White, M. E., et al., *J Neurosci* 18:10366–10374 (1998)). Thus, relatively mature neurons surrounded by diverse glia and possessing large synaptic populations appear to effectively resist uptake and/or accumulation of Aβ1–42. Treatment with integrin antagonists led to substantial intraneuronal buildup of Aβ1–42 and expanded the slice depth and anatomical range over which uptake occurred.

Enhanced Intraneuronal Aβ Levels Upregulate Cathepsin D and Activate Microglia

Enhanced accumulation of Aβ1–42 was accompanied by a marked increase in intraneuronal cathepsin D and activation of microglia. Previous biochemical studies showed that Aβ1–42 causes a modest increase in cathepsin D concentrations in cultured slices (Hoffman, K. B., et al., *Neurosci Lett* 250:75–78 (1998)); the present results indicate that this effect is markedly enhanced when the uptake and/or accumulation of amyloid is increased. Experimentally induced lysosomal dysfunction causes a rapid increase in the concentration and activity of cathepsin D in cultured slices (Bednarski, E., and Lynch, G., *Neuroreport* 9:2089–2094 (1998); Bi, X., et al., *J Neurochem* 74:1469–1477 (2000)) and studies with dissociated neurons have shown that A,β1–42 triggers the release of the protease into the cytoplasm (Yang, A. J., et al., *J Neurosci Res* 52:691–698 (1998)). In addition to showing that internalized Aβ causes significant intracellular disturbances, the increases of cathepsin D observed herein suggest links between Aβ sequestration and AD pathologies. That is, increases in Cathepsin D occur in AD-vulnerable neurons in advance of overt pathology (Cataldo, A. M., et al., *Neuron* 14:671–680 (1995)) and correlate, on a cell-by-cell basis, with the presence of neurofibrillary tangles and decreases in synaptophysin in field CA1 of AD brains (Callahan, L. M., et al., *J Neuropathol Exp Neurol* 58:275–87 (1999); Ginsberg, S. D., et al., *Ann Neurol* 48:77–87 (2000)).

The microglial reaction observed in the present study may constitute a second link between effects of Aβ sequestration and AD. Inflammation, including microglial activation, is now recognized as an important component of AD-related pathology [see (Akiyama, H., et al., *Neurobiol Aging* 21:383–421 (2000)) for review]. Amyloid plaques are typically surrounded by reactive microglia (Perlmutter, L. S., et al., *Neurosc Lett* 119:32–36 (1990); Cras, P., et al., *Brain Res* 558:312–314 (1991)) as are Aβ deposits in brains of 12 month old AβPP(V717F) transgenic mice (Murphy, G. M. J., et al., *Am J Pathol* 157:895–904 (2000)). In the instant invention, microglia were similarly spatially associated with Aβ, but in this instance, as described, Aβ1–42 was accumulated intraneuronally. This suggests that internalized Aβ triggers pathogenic responses in neurons, resulting in the release of signals that activate microglia. Finally, the presence of both microglial activation and cathepsin D induction in brain tissue with heightened Aβ uptake, support the hypothesis that the low levels of uptake occurring with exposure to Aβ peptide alone may be responsible for the relatively modest effects of exogenous Aβ on complex brain systems (Games, D., et al., *Neurobiol Aging* 13:569–576 (1992); Podlisny, M. B., et al., *Am J Pathol* 142:17–24 (1993); Bahr, B., et al., *J Comp Neurol* 397:139–147 (1998); Harris-White, M. E., et al., *J Neurosci* 18:10366–10374 (1998)).

It has generally been accepted that insoluble aggregated fibrils consisting of Aβ1–42 are the neurotoxic components in AD pathogenesis. However, in vitro experiments revealed that extracellular Aβ concentrations, even in familial AD (Suzuki, N., et al., *Science* 264:1336–1340 (1994); Kuo, Y. M., et al., *J Biol Chem* 271:4077–4081 (1996); Scheuner, D., et al., *Nat Med* 2:864–870 (1996)), are far below what is necessary for fibrillar aggregation (Harper, J. D., and Lansbury, P. T. J., *Annu Rev Biochem* 66:385–407 (1997)). On the other hand, intracellular Aβ concentrations may reach amyloidogenic levels (Yang, A. J., et al., *J Neurosci Res* 52:691–698 (1998); Gouras, G. K., et al, *Am J Pathol* 156:15–20 (2000); Walsh, D. M., et al., *Biochemistry* 39:10831–10839 (2000)) through overproduction, enhanced internalization, or decreased degradation. High concentrations of intracellular Aβ could aggregate, cause neurodegeneration, and "seed" mature neuritic plaques. Intraneuronal initiation of Aβ toxicity is supported by recent transgenic studies showing that the peptide can cause synaptic degeneration in the absence of extracellular plaque formation (Hsia, A. Y., et al., *Proc Natl Acad Sci USA* 96:3228–3233 (1999); Mucke, L., et al., *J Neurosci* 20:4050–8 (2000)). Disassociation of extracellular Aβ deposition and functional impairment was also observed in recent vaccine studies: while immunization with Aβ significantly blocked learning and memory deficits in transgenic mice, it only modestly decreased extracellular Aβ deposits (Morgan, D., et al., *Nature* 408:982–85 (2000)).

NMDA Receptors are Involved in Integrin Antagonist-induced AβUptake and Correlates The present experiments also demonstrate that NMDA receptors have a potent effect on Aβ uptake. NMDA receptors admit calcium into neurons (Burnashev, N., et al., *Science* 257:1415–1419 (1992)) and are coupled to the intracellular actin network (Dunah, A. W., et al., *Brain Res Mol Brain Res* 79:77–87 (2000)). Calcium is critical to endocytosis (Seiler, C., and Nicolson, T., *J Neurobiol* 41:424–434 (1999)) while the actin network appears to be a central component of endocytosis across cell types (Gottlieb, T. A., et al., *J Cell Biol* 120:695–710 (1993)). Moreover, recent studies have shown that activation of NMDA receptors by synaptically released glutamate promotes clathrin-coated pit endocytosis in cultured neurons (Carroll, R. C., *Proc Natl Acad Sci USA* 96:14112–14117 (1999); Beattie, E. C., et al., *Nat Neurosci* 3:1291–300 (2000); Ehlers, M. D., *Neuron* 28:511–25 (2000)).

The actions of the NMDA receptor antagonist on the uptake of Aβ were paralleled by its effects on Aβ-induced increases in cathepsin D and microglial activation. This constitutes strong evidence that both of these pathogenic effects were secondary to intraneuronal accumulation of Aβ. The results also raise the possibility that a gradual loss of integrin-mediated adhesion with age results in enhanced contributions of the NMDA receptor to Aβ internalization and, hence, in a slow increase in amyloid-triggered pathogenesis. There is evidence that integrin mediated adhesion changes with age in peripheral cells (Le Varlet et al., 1998; Labat-Robert, 1998) but similar analyses have not been conducted for brain; comparable age-effects at brain synapses could result in enhancement of NMDA receptor driven effects of the type seen in integrin antagonist-treated slices herein.

The above results provide, among other things, the following. 1) Sequestration of and/or accumulation of and/or uptake of Aβ can be induced in culture slices in a medium which modulates integrins and/or integrin receptors. 2) Incubating cultured hippocampal slices with an agent which modulates integrins and/or integrin receptors for 4 days resulted in the sequestration of and/or accumulation of and/or uptake of Aβ that was far more significant than in hippocampal slices not treated with an agent which modulates integrins and/or integrin receptors. 3) Immunocytochemical analysis revealed that the hippocampal slices that were treated with an agent which modulates integrins and/or integrin receptors had enhanced levels of cathepsin D when compared to hippocampal slices not treated with an agent which modulates integrins and/or integrin receptors. 4) Activation of microglia was significantly greater in hippocampal slices that were treated with an agent which modulates integrins and/or integrin receptors when compared to hippocampal slices not treated with an agent which modulates integrins and/or integrin receptors. 5) Contacting the brain cells with antagonists to glutamate receptors, such as the NMDA-type glutamate receptor, significantly attenuated any and/or all of the effects triggered by contacting the slices with agent(s) which can modulate integrins and/or integrin receptors.

Thus, the present invention provides an assay system wherein the levels of sequestration of and/or accumulation of and/or uptake of Aβ, and/or lysosomal dysfunction, and/or microglia activation have been significantly induced in brain cells. Moreover, the present invention provides clear evidence, for the first time, for the relationship between integrins and/or integrin receptors, and the sequestration of and/or accumulation of and/or uptake of Aβ, one of the major pathologies in neurodegenerative diseases such as Alzheimer's disease. The location of the sequestration of and/or accumulation of and/or uptake of Aβ, and/or lysosomal dysfunction, and/or microglia activation corresponds to that in tissues from Alzheimer's disease patient.

Among other things, the present invention provides that the sequestration of and/or accumulation of and/or uptake of Aβ, and/or lysosomal dysfunction, and/or microglia activation can be induced in brain cells by contacting the brain cells with a medium that modulates integrins and/or integrin receptors. Moreover, the present results demonstrated that contacting such tissue with antagonists to glutamate receptors in brain, such as the NMDA receptor, can significantly attenuate the tissue's susceptibility to Aβ and its associated pathologies. These results significantly extend the range of neurodegenerative disease features that can be induced in brain cell culture.

In vitro and in vivo tests have demonstrated that amyloid plays an integral role in the pathogenesis of neurodegenerative disease. Thus, not wishing to be bound by a theory, the uptake and/or internalization of amyloid could be a key factor in the pathologies associated with such diseases, and therefore the inhibition of amyloid internalization and/or uptake by the application of an antagonist to glutamate receptors may be a viable therapeutic option for diseases and disorders comprising pathologies related to amyloid. These results significantly extend the range of neurodegenerative disease features that can be induced and/or inhibited in brain cells.

EXAMPLE 2

An embodiment of the invention drawn to a pharmaceutical composition and the use of that composition to treat neurodegenerative diseases such as Alzheimer's disease. The composition alleviates the symptoms of characteristics associated with Alzheimer's disease such as intracellular uptake of amyloid protein, amyloid accumulation or plaque formation, A patient in need of intervention for Alzheimer's disease is selected based on currently used diagnostic guidelines and evaluation criteria such as those detailed: by the National Institute of Neurological and Communicative Disorders and Stroke-Alzheimer's Disease and related Disorders Association (NINCDS-ADRDA), the Alzheimer's Disease section found in the Diagnostic and Statistical Manual of Mental Disorders 4$^{th}$ edition (DSM-IV), by the National Institute of Neurological Disorders and Stroke and the Association pour la REcherche et l'Enseignement en Neurosciences (NINDS-AIREN), and/or by the California Alzheimer's Diseases Diagnostic and Treatment Centers (CAD-DTC).

After evaluation the patient is treated with a pharmaceutical composition comprising an appropriate amount of an NMDA antagonist such as magnesium, ketamine, dextromethorphan, amantadine, dexanabinol, AP3, AP5, AP6, AP7, 4C3HPG, 4CPG, CGS 19755, chlorophenylglutamic acid, CPP, MK-801, PCP, ibogaine, noribogaine, ienprodil, flupirtine, selfotel, D-CPP-ene, procyclidine, trihexyphenidyl, CP-101606, CP-GVI150526, AR-R15896AR, NPS 1506, NPC 12626, LY274614, LY 2835959, SDZ 220-040, SDZ 220-040, SDZ 220-581, SDZ 221-653, and similar compounds, based on the body weight of the patient and with an appropriate carrier or excipient.

Those of skill in the art would be able to obtain general and source information for the above compounds. Specific information several of these antagonists can be found in; *Curr. Drug Targets* 2:241–271 (2001), Rao et al., *Brain Res.* 911:96–100 (2001) (memantine), Mueller et al., *Ann. N.Y. Acad Sci.* 890:450–457 (1999), Chazot *Curr. Opin. Investig Drugs* 1:370–374 (2000) and Proescholdt et al., *Brain Res.* 904:245–251 (2001) (ketamine).

Specific commercial sources for AP5 and MK801 are Slgman and Research Biochemical Incorporation respectively.

Following a period of treatment the patient is reevaluated and treatment is continued with increasing or decreasing amounts of the pharmaceutical composition.

Evaluations are carried out using techniques known to those of skill in the art and may include MRI (Selkoe, D. *Nat. Biotechnol.* 18:823–824, 2000; Fox, N. et al., *Nat. Med.* 6:20–21, 2000), PET, Electroencephalogram analysis and use of certain cognitive tests (Clinical Demention Rating (DR), Morris, J. *Neurology* 43:2412–2414, 1993).

The present invention provides novel materials, such as brain cells and methods for producing the cells which can be used as a model of neurodegenerative diseases, including Alzheimer's disease. Additionally, methods of treating neurodegenerative diseases are provided. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, applicants do not admit any particular reference is "prior art" to their invention.

What is claimed is:

1. A method for determining the effect of a substance on sequestration, uptake or accumulation of amyloid in brain cells, said method comprising:

(A) exposing brain cells in vitro to an integrin antagonist, wherein said antagonist is selected from the group consisting of function blocking anti-β5 subunit integrin antibody, function blocking anti-β1 subunit integrin antibody, an RGD peptide capable of modifying integrin adhesion, RGDS peptide, GRGDS peptide, GRGDSP peptide, GRGDTP peptide and echistatin, (B) maintaining said cells for a time sufficient to induce sequestration, uptake or accumulation of amyloid in said cells as a result of said antagonist, (C) adding said substance before, during and/or after said exposing or maintaining; and (D) determining whether the presence of said substance has an effect on said antagonist induced sequestration, uptake or accumulation of amyloid.

2. The method of claim 1, wherein sequestration, uptake or accumulation of amyloid increases.

3. The method of claim 2, wherein said increase is at least about 10% compared to a control.

4. The method of claim 1, wherein at least one of said sequestration, uptake or accumulation of amyloid decreases.

5. The method of claim 4, wherein said decrease is at least about 10% compared to a control.

6. The method of claim 1, wherein the brain cells are in the form of a brain slice.

7. The method of claim 6, wherein the brain slice is a hippocampal slice, an entorhinal cortex slice, an entorhino-hippocampal slice, a neocortex slice, a hypothalamic slice, or a cortex slice.

8. The method of claim 1, wherein said antagonist is said function blocking anti-α5 subunit integrin antibody or said function blocking anti-β1 subunit integrin antibody.

9. The method of claim 1, wherein said antagonist is said RGD peptide, RGDS peptide, GRGDS peptide, GRGDTP peptide, GRGDSP peptide or echistatin.

10. The method of claim 1, wherein the amount of sequestration of amyloid, accumulation of amyloid, or uptake of amyloid, is determined visually.

11. The method of claim 1, wherein the amount of sequestration of amyloid, accumulation of amyloid, or uptake of amyloid is measured using a capture reagent.

12. The method of claim 10, wherein the capture reagent is an antibody that binds to amyloid.

13. The method of claim 1 wherein said cells are apolipoprotein E deficient brain cells or apolipoprotein E4 containing brain cells cultured in a medium which selectively increases sequestration of and/or accumulation of and/or uptake of amyloid, and/or lysosomal dysfunction, and/or microglia activation in the brain cells, wherein the brain cells comprise an increased amount of sequestration of and/or accumulation of and/or uptake of amyloid, and/or lysosomal dysfunction, and/or microglia activation compared to a control.

14. The method of claim 1 wherein said substance is added prior to exposing said brain cells to said antagonist.

15. The method of claim 1, wherein said substance is added to said brain cells simultaneously with said antagonist.

16. A method for determining whether a substance is capable of inhibiting sequestration, uptake or accumulation of amyloid in brain cells, said method comprising:

(A) exposing brain cells in vitro to an integrin antagonist, wherein said antagonist is selected from the group consisting of function blocking anti-α5 subunit integrin antibody, function blocking anti-β1 subunit integrin antibody, an RGD peptide capable of modifying integrin adhesion, RGDS peptide, GRGDS peptide, GRGDSP peptide, GRGDTP peptide and echistatin, (B) maintaining said cells for a time sufficient to induce sequestration, uptake or accumulation of amyloid one or more characteristics of a neurodegenerative disease in said cells as a result of said antagonist, (C) adding said substance before, during and/or after said exposing or maintaining; and (D) determining whether the presence of said substance inhibits one or more of said characteristics sequestration, uptake or accumulation of amyloid in said cells.

17. The method of claim 16, wherein at least one of said sequestration, uptake or accumulation of amyloid decreases.

18. The method of claim 17, wherein said decrease is at least about 10% compared to a control.

19. The method of claim 16, wherein the brain cells are in the form of a brain slice.

20. The method of claim 19, wherein the brain slice is a hippocampal slice, an entorhinal cortex slice, an entorhino-hippocampal slice, a neocortex slice, a hypothalamic slice, or a cortex slice.

21. The method of claim 16, wherein said antagonist is said function blocking anti-α5 subunit integrin antibody or said function blocking anti-β3 subunit integrin antibody.

22. The method of claim 16, wherein said antagonist is said RGD peptide, RGDS peptide, GRGDS peptide, GRGDTP peptide, GRGDSP peptide or echistatin.

23. The method of claim 16, wherein the amount of sequestration of amyloid, accumulation of amyloid, or uptake of amyloid is determined visually.

24. The method of claim 16, wherein the amount of sequestration of amyloid, accumulation of amyloid, or uptake of amyloid is measured using a capture reagent.

25. The method of claim 24, wherein the capture reagent is an antibody that binds to amyloid.

26. The method of claim 16 wherein said cells are apolipoprotein E deficient brain cells or apolipoprotein E4 containing brain cells.

* * * * *